(12) United States Patent
Chiarello et al.

(10) Patent No.: US 7,319,523 B2
(45) Date of Patent: Jan. 15, 2008

(54) APPARATUS FOR A LIQUID CHEMICAL CONCENTRATION ANALYSIS SYSTEM

(75) Inventors: Ronald Phillip Chiarello, Los Gatos, CA (US); Charles Eric Boyd, San Jose, CA (US); Duncan A. McPhee, Campbell, CA (US)

(73) Assignee: Jetalon Solutions, Inc., Los Gatos, CA (US)

( * ) Notice: Subject to any disclaimer, the term of this patent is extended or adjusted under 35 U.S.C. 154(b) by 18 days.

(21) Appl. No.: 11/235,622

(22) Filed: Sep. 26, 2005

(65) Prior Publication Data

US 2007/0070330 A1    Mar. 29, 2007

(51) Int. Cl.
*G01N 21/00* (2006.01)
*G01N 21/41* (2006.01)

(52) U.S. Cl. .................. 356/436; 356/128; 356/136
(58) Field of Classification Search ........ 356/128–137, 356/445–448, 432–440
See application file for complete search history.

(56) References Cited

U.S. PATENT DOCUMENTS

| | | | |
|---|---|---|---|
| 3,751,672 A * | 8/1973 | Michel et al. .............. 250/552 |
| 4,704,029 A * | 11/1987 | Van Heuvelen .............. 356/39 |
| 4,778,270 A * | 10/1988 | Kinney et al. ................ 356/43 |
| 5,364,510 A | 11/1994 | Carpio |
| 5,442,435 A * | 8/1995 | Cooper et al. .............. 356/133 |
| 5,565,978 A * | 10/1996 | Okubo et al. ............... 356/128 |
| 5,617,201 A | 4/1997 | Kahre |
| 5,898,503 A | 4/1999 | Keller et al. |
| 5,912,456 A | 6/1999 | Melendez et al. |
| 5,922,285 A | 7/1999 | Melendez et al. |
| 5,946,083 A | 8/1999 | Melendez et al. |
| 6,024,923 A | 2/2000 | Melendez et al. |
| 6,045,756 A | 4/2000 | Carr et al. |
| 6,097,479 A * | 8/2000 | Melendez et al. .......... 356/136 |
| 6,111,248 A | 8/2000 | Melendez et al. |
| 6,111,652 A | 8/2000 | Melendez et al. |
| 6,183,696 B1 | 2/2001 | Elkind et al. |
| 6,191,847 B1 | 2/2001 | Melendez et al. |
| 6,239,255 B1 | 5/2001 | Furlong et al. |

(Continued)

FOREIGN PATENT DOCUMENTS

JP    401170838 A  *  7/1989

OTHER PUBLICATIONS

J.E. Geake, C.S. Mill and M.S. Mohammadi, A linear differentiating refractometer, Meas. Sci. Technol., 5th ed., pp. 9, (Feb. 24, 1994).

(Continued)

*Primary Examiner*—Hoa Q. Pham
(74) *Attorney, Agent, or Firm*—Steven D. Hemminger; Akin, Gump, Strauss, Hauer & Feld LLP

(57) ABSTRACT

An apparatus utilizes optical reflectivity (REF) to measure concentrations in liquids. The REF optical system is packaged in a compact and cost-effective form factor. An electronic circuit drives the optical system. The miniaturized REF sensor is situated in an optical-fluidic cell or an optical-fluidic manifold with an optical window in contact with the liquid. Changes in a total internal reflection (TIR) signal are sensitive to temperature and concentration of the liquid. These changes in the TIR signal are used to accurately determine the concentration in the liquid. The liquids may be either static or dynamic.

48 Claims, 32 Drawing Sheets

U.S. PATENT DOCUMENTS

| | | |
|---|---|---|
| 6,267,641 B1 | 7/2001 | Vanell et al. |
| 6,326,612 B1 | 12/2001 | Elkind et al. |
| 6,374,845 B1 | 4/2002 | Melendez et al. |
| 6,386,894 B2 | 5/2002 | Carr |
| 6,401,974 B1 | 6/2002 | Elkind |
| 6,415,235 B1 | 7/2002 | Bartholomew et al. |
| 6,549,276 B1* | 4/2003 | Longtin .................. 356/128 |
| 6,574,575 B2 | 6/2003 | Deng et al. |
| 6,594,018 B1 | 7/2003 | Bartholomew |
| 7,064,816 B2* | 6/2006 | Langenbacher et al. .... 356/128 |
| 7,144,153 B2* | 12/2006 | Sato .................. 374/142 |
| 2005/0046853 A1* | 3/2005 | Sato .................. 356/445 |
| 2006/0094941 A1* | 5/2006 | Cho et al. .................. 600/316 |
| 2006/0158653 A1* | 7/2006 | Chiarello et al. .......... 356/445 |

OTHER PUBLICATIONS

G.H. Meeten and A. N. North, Refractive index measurement of absorbing and turbid fluids by reflection near the critical angle, Meas. Sci. Technol. 6, 6th ed., pp. 8, (Nov. 21, 1994).

Geake, J.E. et al., The Huygens SSP Refractometer, Proceedings, Symposium on Titan, Apr. 1992.

Lorenz, R. D., Raindrops on Titan, Adv. Space. Res., vol. 15, No. 3, pp. (3)317-(3)320, 1995.

* cited by examiner

------- LIQUID FLOW PATH

------- LIQUID FLOW PATH

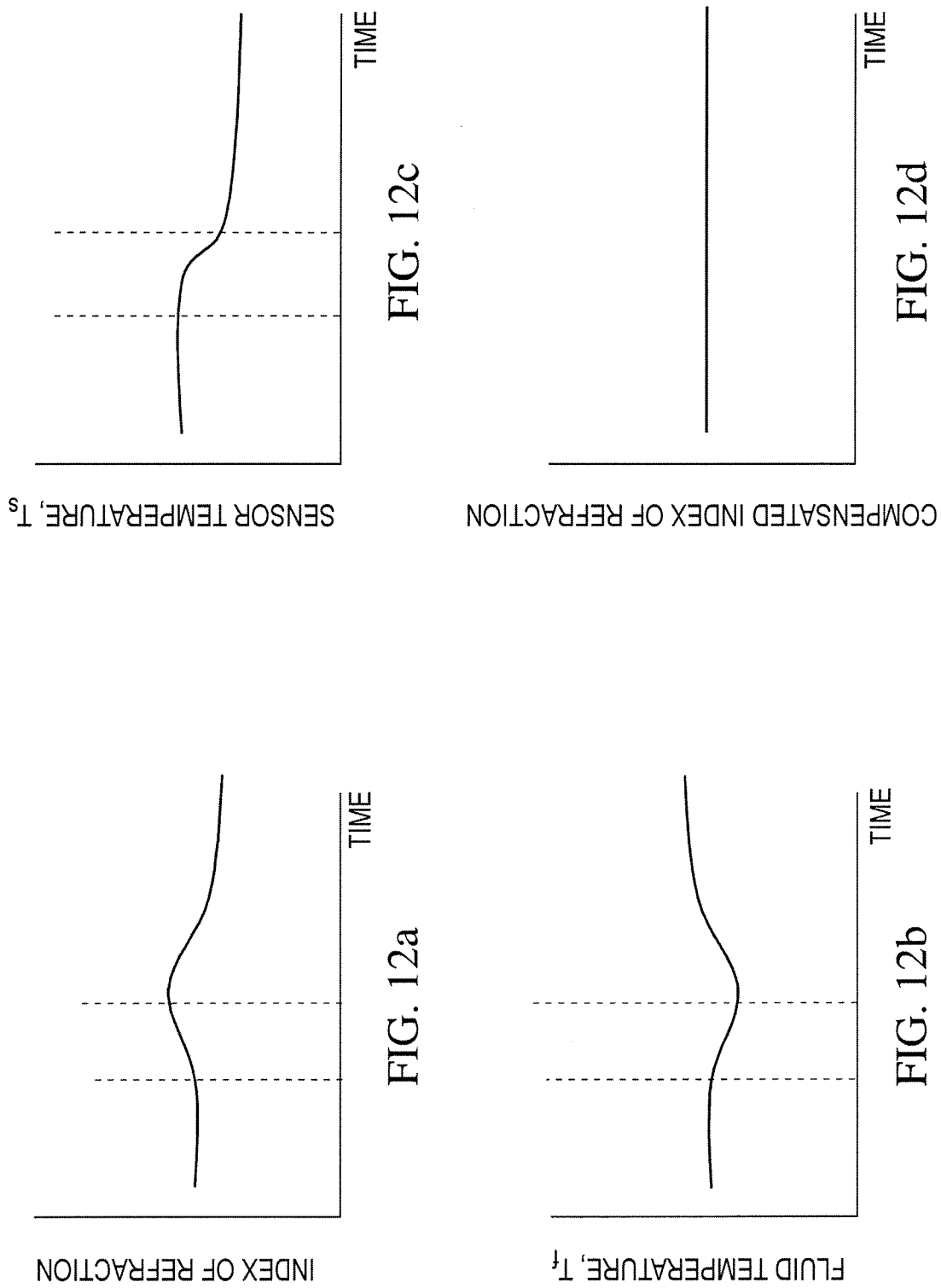

APPARATUS FOR A LIQUID CHEMICAL CONCENTRATION ANALYSIS SYSTEM

BACKGROUND OF THE INVENTION

1. Field of the Invention

The present invention relates to the field of analytical chemical instrumentation utilizing optical sensors and in particular to integrated optical-chemical analytical instrumentation used in the fields of chemical, biochemical, biological or biomedical analysis, process control, pollution detection and control, and other similar areas.

2. Discussion of the Related Art

Referring to FIG. 1, a prior art optical sensor 50 is shown. The optical sensor 50 utilizes optical reflectivity to determine Index of Refraction (IoR). The sensor 50 detects the presence of a sample 40 by using a critical angle to find the sample's Index of Refraction, as shown in Equation 1 below, where $n_2$ is the Index of Refraction of the medium of transmission, $n_1$ is the Index of Refraction of the medium of origin (light transmissive housing 55) and $\theta_c$ is the critical angle.

$$n_1 = n_2 \sin \theta_c \qquad (1)$$

As shown in FIG. 1, the necessary electro-optical components are contained within an encapsulating light transmissive housing 55. Light source 57 emits electromagnetic radiation, or light rays 59, 60, and 61 toward a reflective mirrored surface 62. The light rays 59, 60, 61 then travel through the housing 55 in the direction of sensing surface 64 which forms the interface between the sensor 50 and the sample 40. Thus the sensing surface is in direct contact with the sample.

The plurality of light rays 59, 60, and 61 strike the sensing surface 64 at a range of angles. For angles of incidence smaller than the critical angle 75, a portion of the light is refracted into the sample 40 resulting in an overall loss. This is illustrated by refractive ray 63 which travels into the sample and reflected ray 65 which reflects into the housing 55 at angle 74.

At the critical angle 75, a light ray 60 reflects along the sensing surface 64 at a 90 degree angle of refraction minimizing the overall light loss into sample 40. Thus, a critical angle 75 can be measured as the angle measured between the incident light ray 67 and the normal to the sensing surface 64. For angles of incidence larger than the critical angle 75, such as 76, the incident ray 69 is totally internally reflected within housing 55, with no refracted component, and its full intensity is therefore directed toward photodetector 90. This total internal reflection can only occur when light originates in a medium of a higher Index of Refraction.

It should be noted, however, that the Index of Refraction of the housing material may be lower than the sample 40. In such a configuration, the sensor 50 can be used to render a threshold level of Index of Refraction eliminating a range less than that of the housing material.

For optical radiation, a suitable photodetector 90 is the TSL213, TSL401, and TSL1401 (manufactured by Texas Instruments Inc. Dallas, Tex.), with a linear array of resolution n×1 consisting of n discrete photo sensing areas, or pixels. Light energy striking a pixel generates electron-hole pairs in the region under the pixel. The field generated by the bias on the pixel causes the electrons to collect in the element while the holes are swept into the substrate. Each sensing area in the photodetector 90 thereby produces a signal on an output with a voltage that is proportional to the intensity of the radiation (60, 65, 70) striking the photodetector 90. This intensity and its corresponding voltage are at their maxima in the total internal reflection region.

Various means of photodetection are contemplated including an n×1 cell photodetector such as the TSL213, TSL401, and TSL1401. In addition, a single cell photo resistor, bolometer, positive sensitive detector, pyrolectric device as well as other devices may be used.

As described, a range of angles of the reflected light rays are projected onto photodetector 90. The critical angle is marked by a transition from high to low intensity. The output, representing bit level data from the photodetector 90, is transmitted within housing 55 via interface 92 to a signal processing unit 95 for further qualitative and/or quantitative analysis. The signal processing unit 95 may provide the necessary interface control signals, such as clock line and serial input, for protocol communications with the photodetector 90. Signal processing unit 95 may be used increasing the sensor's resolution over that obtained by the photodetector 90 pixel resolution. The use of the signal processing unit 95 is optional.

When used, signal processing unit 95 is preprogrammed to analyze and characterize the intensity, occurrence, and timing of light rays 60, 65, and 70 to obtain qualitative and quantitative information about the sample 40. For example, signal processing unit 95 can be preprogrammed to determine the total amount of time that sample 40 is within a given proximity of the sensor 50. Also, signal processing unit 95 can be preprogrammed to determine the frequency of sample 40 over a given period of time.

Output data from signal processing unit 95 may be transmitted via interface 96 to a secondary system, such as a computer, hand-held meter, calculator, printer, logic analyzer, or other similar system (not shown). The interface 96 comprises a plurality of conductive pins, giving the sensor a platform similar to an integrated circuit package.

Sensor 50 may also include a temperature sensor 98 within the housing 55. Temperature sensor 98 produces an electrical signal indicative of the temperature of the sensor surface 64 during operation thereof. This temperature signal may be relayed to signal processing unit 90 via interface 97. Temperature data can be utilized to compensate for apparent changes in the measured Index of Refraction as a result of changes in the operating temperature.

A filter may be used to screen out radiation at wavelengths other than wavelengths produced by light source 57. This filter (not shown) may overly photodetector 90 and serves to pass radiation at the wavelengths produced by light source 57 to photodetector 90. As such, the filter eliminates unwanted noise caused by other radiation sources in proximity to the sensor 50. One suitable filter is the plastic filter material marketed by Polaroid Corporation and known as XR-84. This material is especially suitable for passing infrared radiation and blocking visible radiation.

An alternative to utilizing a filter is to utilize a plastic or epoxy material for the housing 50 which is transparent to wavelengths produced by the light source 57 and opaque to frequencies outside the desired frequency range of interest for a given sensor/sample combination. Likewise, an absorbing die can be enclosed in the housing to achieve the same function.

Referring to FIG. 2, a prior art optical sensor 100 is shown. This prior art sensor can be seen to incorporate the same filter features discussed above. The electro-optic components of the optical sensor 100, including light emitting diode 120, photodetector array 110, and temperature sensor 125, may be encapsulated within a trapezoidal-shaped optical housing 150 and coupled to an interior surface 161 of a substrate 160. A plurality of conductive leads 165 are coupled to an exterior surface 162 of the substrate 160. A memory chip 163 is included. An optical window 140 made from glass is attached to the optical housing 150 to form part of sensing surface 145.

SUMMARY OF THE INVENTION

The present invention marks a step forward for concentration analysis for liquid chemicals, in that it is a real-time, cost-effective system packaged in a compact form factor that is conveniently integrated into many applications. In the present invention, optical reflectivity (REF) is used to determine the Index of Refraction (IoR) and thereby the chemical concentration of the liquid chemical under analysis.

The present invention consists of a miniaturized fully-integrated optical subsystem, an optical-fluid cell, and an independent electronic circuit. The present invention brings several innovations to concentration analysis made by Index of Refraction.

First, Index of Refraction measurements in themselves do not provide information on chemical concentration. The present invention includes a firmware algorithm (on board an electronic circuit) and a software program for a step-wise calibration method that directly correlates IoR measurements to chemical concentration.

Second, the optical-fluidic cell of the present invention provides for analysis of liquids under both static and dynamic conditions, uses an optically transparent sapphire window that is placed in direct contact with the liquid under analysis and has a refined fluid dynamic design to provide dynamic mixing of solutions and mixtures at the sensing surface. In accordance with the present invention, sapphire provides superior chemical and mechanical integrity and durability over prior art IoR sensors. Dynamic mixing at the sensor surface provides increased resolution and accuracy for concentration analysis. An innovation over the prior art is to place an optical sapphire window in contact with the liquid under analysis. Sapphire has a hardness of 9 (only diamond is harder) and is resistant to chemical attack. This improvement over prior art sensors improves the optical, chemical and mechanical integrity of the sensing surface and provides increased durability, accuracy and resolution.

Third, IoR measurements are highly sensitive to temperature changes of both the liquid under analysis and to electro-optical components. The present invention uses a two-point temperature measurement system and a temperature compensation method via a firmware algorithm on-board the electronic circuit to automatically perform temperature compensation for concentration analysis in real-time. The temperature compensation apparatus and method afford the present invention real-time (~10 mS) measurement with high resolution ($\geq 0.01\%$ concentration) and high accuracy.

Fourth, another innovation of the present invention is a three stage-signal processing and signal averaging. This innovation also contributes to real-time measurement, high resolution and high accuracy.

Fifth, yet another innovation is a method for automatic compensation of variations in the brightness of the light source as a function of light source temperature. This innovation contributes to real-time measurement, high resolution and high accuracy.

Sixth, another innovation is that the present invention need not determine the critical angle in order to determine IoR and thereby chemical concentration. The present invention uses numerical methods to determine the Mass Moment (MM) of the first numerical derivative of the measured optical reflectivity. The MM value is input into a calibration method that is used to determine IoR and thereby chemical concentration.

In summary, the present invention incorporates several innovations in both apparatus and methodologies to provide significant improvement over prior art IoR sensors.

BRIEF DESCRIPTION OF THE DRAWINGS

FIG. 12*a* illustrates the measured Index of Refraction as a function of time according to an embodiment of the present invention;

FIG. 12*b* illustrates the measured fluid temperature as a function of time according to an embodiment of the present invention;

FIG. 12c illustrates the measured sensor temperature as a function of time according to an embodiment of the present invention;

FIG. 12d illustrates the compensated Index of Refraction as a function of time according to an embodiment of the present invention;

DETAILED DESCRIPTION

According to embodiments of the present invention, a chemical concentration analysis sensor and system for liquids are described. In the preferred embodiment, the analysis sensor is used in situ and at the point-of-use. The analysis sensor and system are applicable to many liquid chemical applications. The sensor analyzes concentration for acids, bases, aqueous-based liquids, solvents, slurries, and ultra-high purity, caustic and corrosive liquids. The invention is useful in manufacturing facilities, water treatment and water recycling/reclaim systems (both industrial and municipal), medical applications, and ground and surface water sources.

In various embodiments, the invention can be integrated into liquid recycling systems, municipal water treatment facilities and into small scale at home water treatment systems. The present invention may be connected to a flowing liquid via input and output lines, immersed into a static reservoir or injected with a sample of a liquid. The analysis system provides concentration information in real-time (0.001-1 seconds), has a compact form factor (<2"× 2"×1") and a concentration sensitivity at or below 0.01%. The analysis system has capabilities as both a monitoring system and as a closed-loop control system for interface with actuators for liquid chemicals such as pumping systems, diverting systems, variable flow valves, waste treatment systems, etc.

Figure 1:
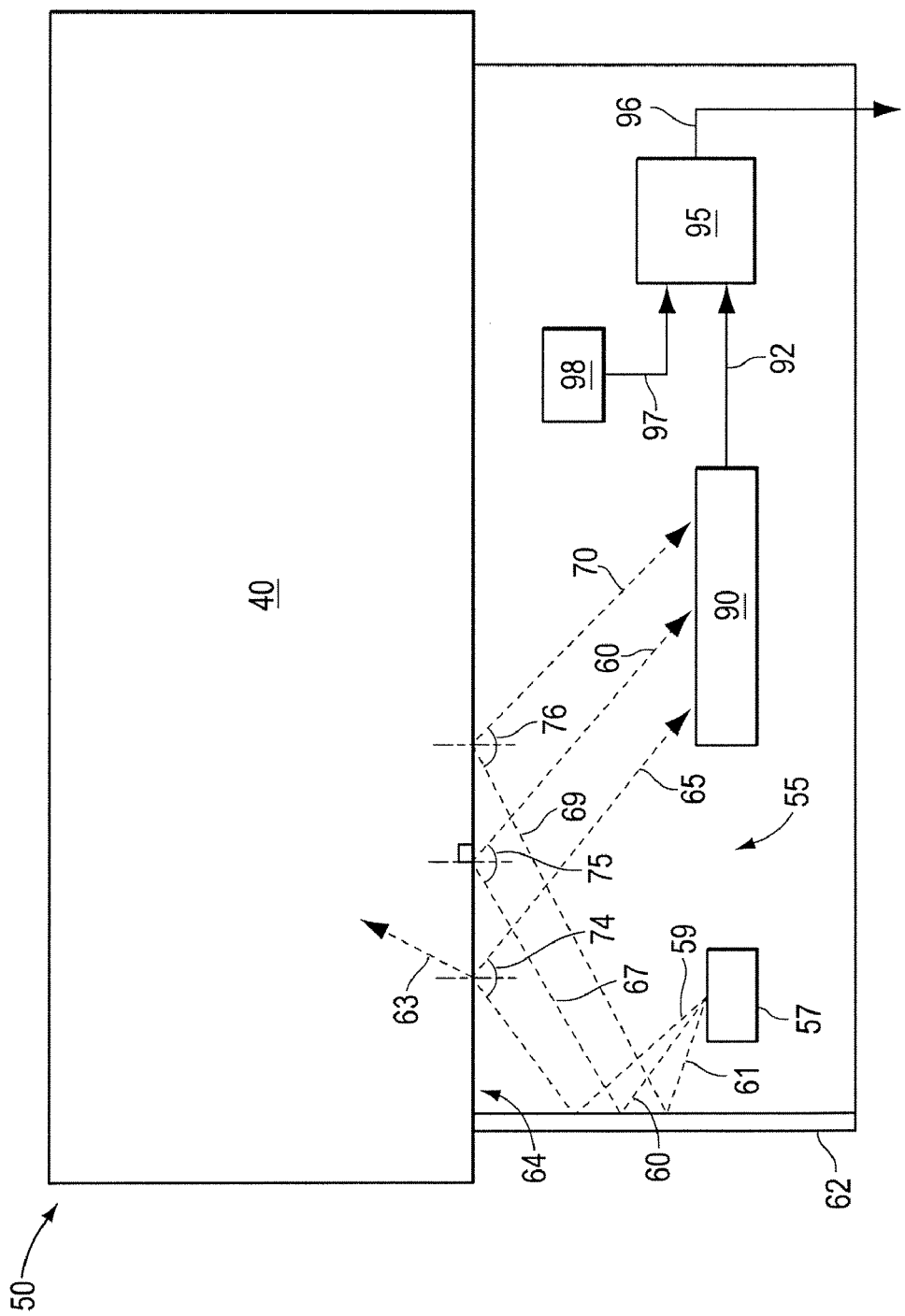
FIG. 1 illustrates a prior art sensor.
Figure 2:
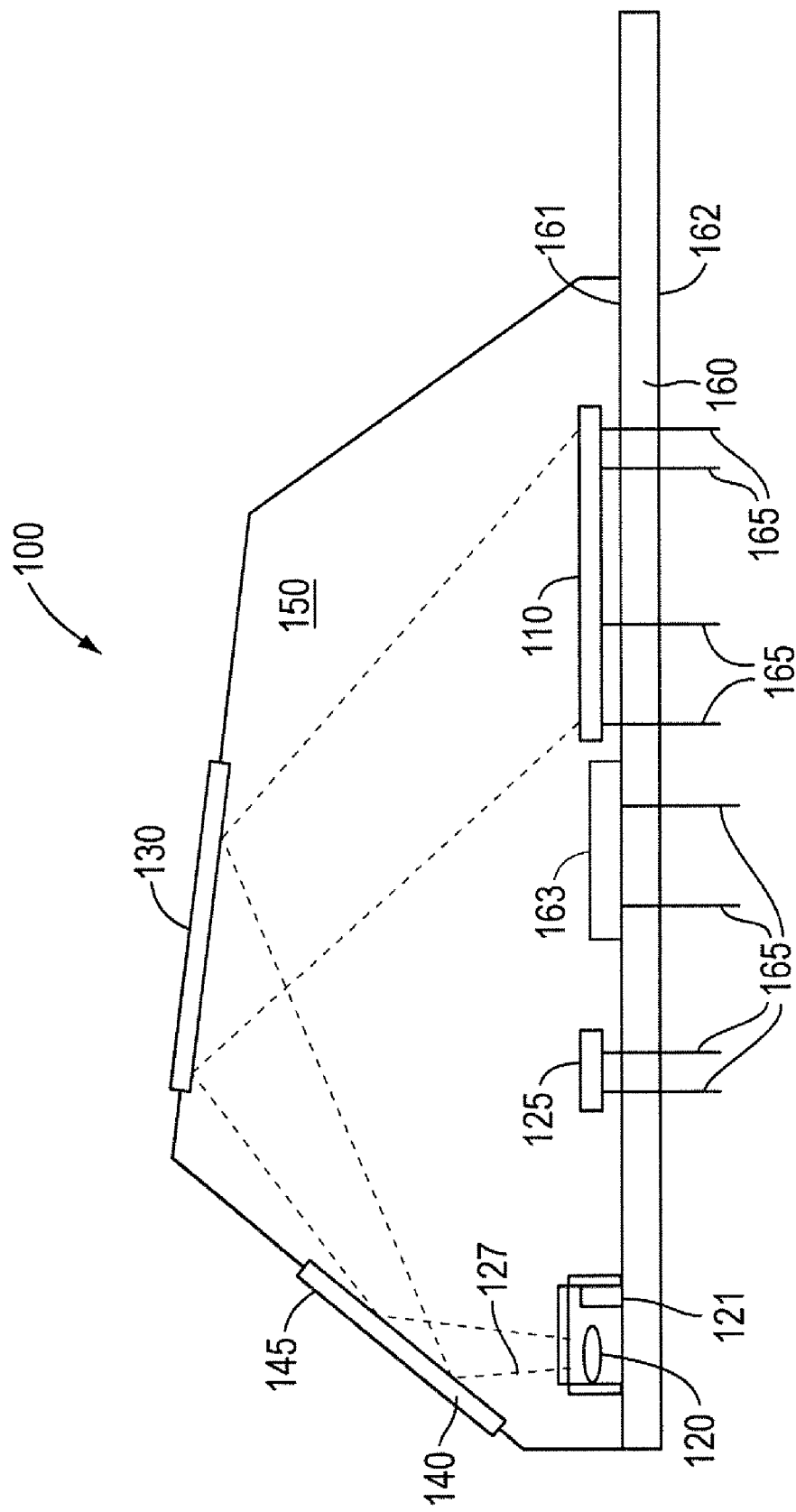
FIG. 2 illustrates a prior art sensor.
Figure 3:
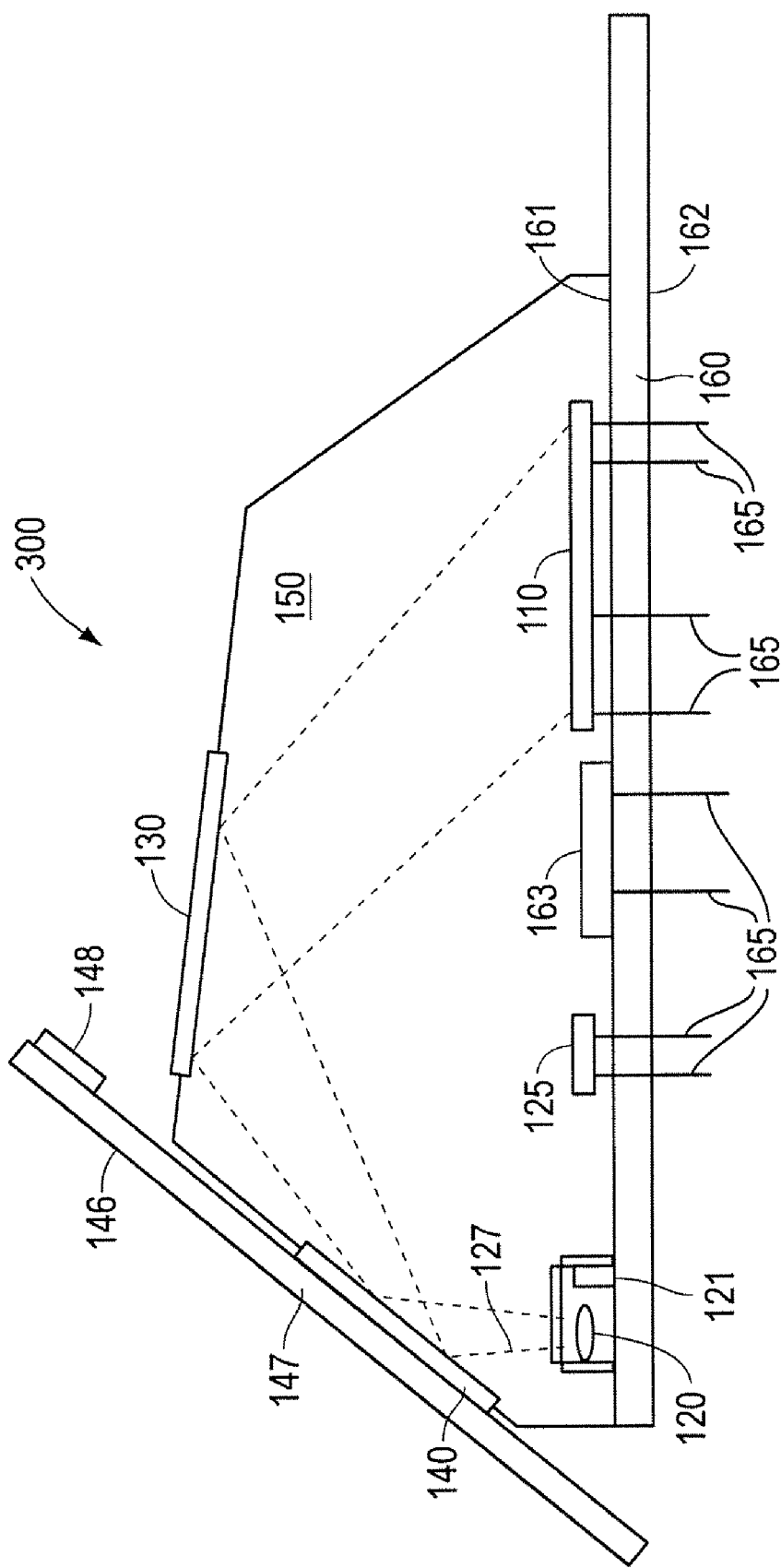
FIG. 3 illustrates a preferred embodiment of the optical sensor.
Figure 4A:
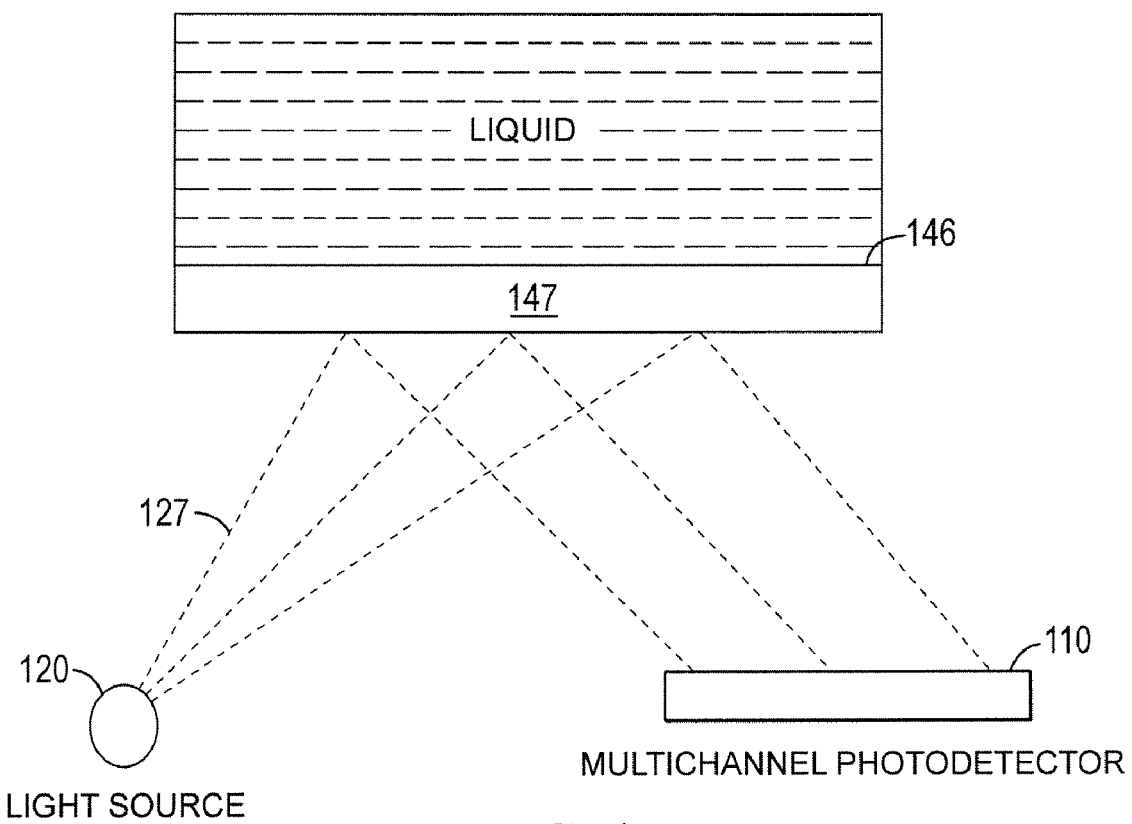
FIG. 4*a* illustrates an optical reflectivity geometry and a principle of operation of the present invention.
Figure 4B:
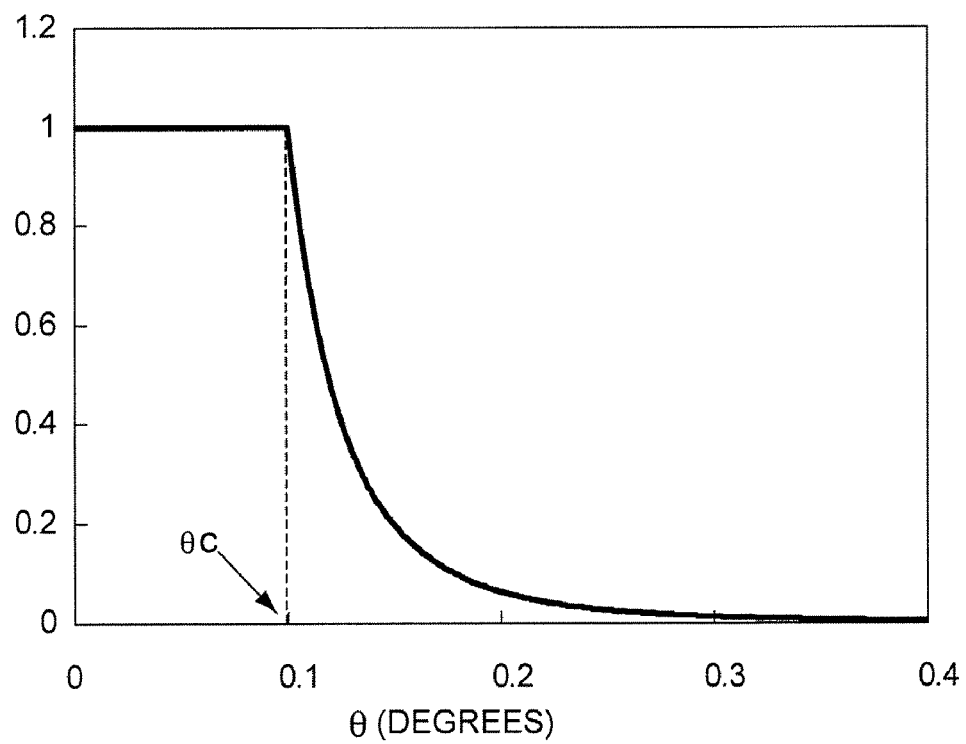
FIG. 4*b* illustrates optical reflectivity data according to an embodiment of the present invention.

Referring to FIG. 3 and FIG. 4a, the principle of operation of the optical sensor 300 of the present invention utilizes optical reflectivity (REF). Light emitting from a light source 120 is incident upon a sapphire window 147 that is in contact with a liquid under analysis. In accordance with the present invention, the liquid under analysis may be static or flowing. Light rays reflect from the interfaces, including the window 147 and the sensing surface at the window/liquid interface 146 onto a multi-channel photo-detector 110. FIG. 4b illustrates an example of optical reflectivity data generated using the REF geometry. The reflectivity data is sensitive to the optical density change across the window-liquid interface 146. Accordingly, the optical density of the liquid in contact with the window 147 is directly related to the measured reflectivity. Since optical density is directly related to Index of Refraction, the Index of Refraction and thereby the concentration of the liquid in contact with the window 147 is determined from the optical reflectivity data by using the apparatus and methods described herein. In accordance with the preferred embodiment of the present invention, the main elements of which include, but may not be limited to in other embodiments, a sensor head, electronic circuit, a cable that connects the sensor head to the electronic circuit, and a firmware algorithm or algorithm that operates the sensor head and control data acquisition and data reporting. The algorithm includes numerical methods to extract Index of Refraction and thereby chemical concentration from reflectivity data. The algorithm also utilizes numerical operations on the "raw" data signal to put the raw data signal into the proper form for analysis. These numerical operations include, but may not be limited, background subtraction and normalizations. The sensor head consists of a miniaturized, fully integrated optical sensor 300 that is packaged into an optical-fluidic cell (OFC) or optical-fluidic manifold (OFM). Referring to FIGS. 6a-d, examples of manifestations of the OFC and OFM for the present invention are illustrated. All of these manifestations are useful in the present invention.

Referring to FIG. 3, the REF geometry is accomplished in a miniaturized, fully integrated optical sensor 300. The miniaturized and integrated optical sensor 300 includes a light source 120, a thermistor 125, and a multi-channel photon detector 110 coupled to a substrate or a printed circuit board (PCB) 160, a second thermistor 148 on the sensor window 147, a mirror 130, a glass (or other appropriate material) window 140 (optional), and the optical window 147 made of a dielectric material, for example, sapphire, quartz, glass, or a similar appropriate dielectric material. A memory chip 163 (optional) and a polarizer 121 (optional) may also be included. The electro-optic components of the optical sensor 300, including light source 120, multi-channel photon detector 110, and thermistor 125 may be encapsulated within a trapezoidal-shaped optical housing 150 and coupled to an interior surface 161 of the substrate or the printed circuit board (PCB) 160. A plurality of conductive leads 165 may be coupled to an exterior surface 162 of the substrate 160.

In the preferred embodiment of the present invention, the light source 120 is a light emitting diode (LED) and the sensor window 147 is sapphire. The second thermistor 148 may be attached to the front or back of the sapphire window for convenience. The second thermistor 148 may also be placed inside the window 147 or in contact with the liquid under analysis at or near the sensing surface 146.

In the present invention, the optical window 147 is placed in direct contact with the liquid under analysis. The window 147 may be made of any dielectric material, with appropriate optical properties, including sapphire, quartz, borosilicate glass or other suitable materials. In the preferred embodiment of the present invention a window 147 made of sapphire is placed in contact with the liquid under analysis. In the preferred embodiment of the present invention, sapphire is specifically selected as the window 147 material due to its superior properties including; mechanical strength, resistance to chemical attack and scratching, durability, optical quality, strength under pressure, machinability and availability. In accordance with the present invention, the optical window 147 can be adhered via an optical epoxy (or other optically appropriate material) directly to the optical sensor 300 housing or to a glass (or other appropriate material) window 140. Also, in accordance with the present invention, the sapphire window may be coated with a thin layer (~20-100 Å) of a material of sufficiently low density to allow light from the light source 120 to pass completely through it into the liquid under analysis. In accordance with the present invention, the purpose of the thin coating is to further protect the window surface from damage or deterioration and therefore extend the useful life of the optical sensor 300.

Figure 5:
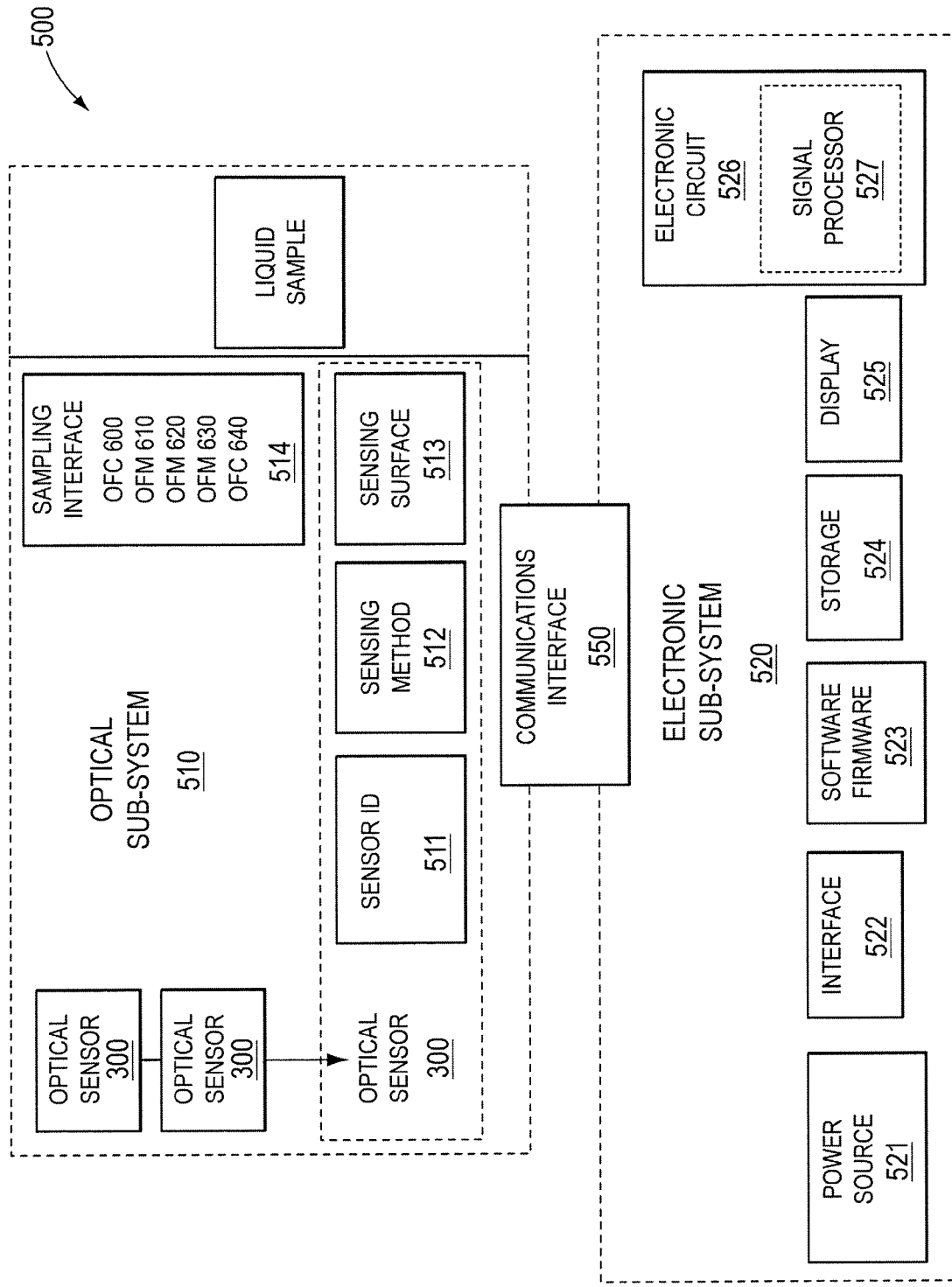
FIG. 5 illustrates a block diagram of a liquid concentration analysis system according to an embodiment of the present invention.

Referring to FIG. 5, an analysis system 500 according to embodiments of the present invention includes an optical sub-system 510 including at least one optical sensor 300, an optical-fluidic cell (OFC) 600 (see FIG. 6*a*) or optical-fluidic manifold (OFM) 610-630 (see FIGS. 6*b-d*), and an electronic sub-system 520 including an electronic circuit 526.

The optical sub-system 510 of the analysis system 500 may include a plurality of optical sensors 300 each having a sensor ID 511 such as a barcode, RF tag or other optical sensor specific identifier to identify a specific optical sensor in question. The sensor ID 511 provides information identifying an optical sensor 300 that is location and/or sample specific depending on the particular sensor application. A sample specific optical sensor 300 can be so labeled via sensor ID 511 permitting electronic sub-system 520 to determine the location of the optical sensor 300 and, if desired, the specific sample which the individual optical sensor 300 is designed to detect. In an embodiment of the present invention, a plurality of optical sensors 300 can be placed in a remote field or facility, or combination thereof and the location and sample type determined via sensor ID 511. By including sensor ID 511 on a plurality of optical sensors 300 on or in the optical sub-system 510, a distributive network of optical sensors 300 can be obtained. Accordingly, a plurality of sensor ID 511 types are possible, including a barcode, radio frequency tag, color code, a label, electronic signature or memory stored identifier.

Figure 6A:
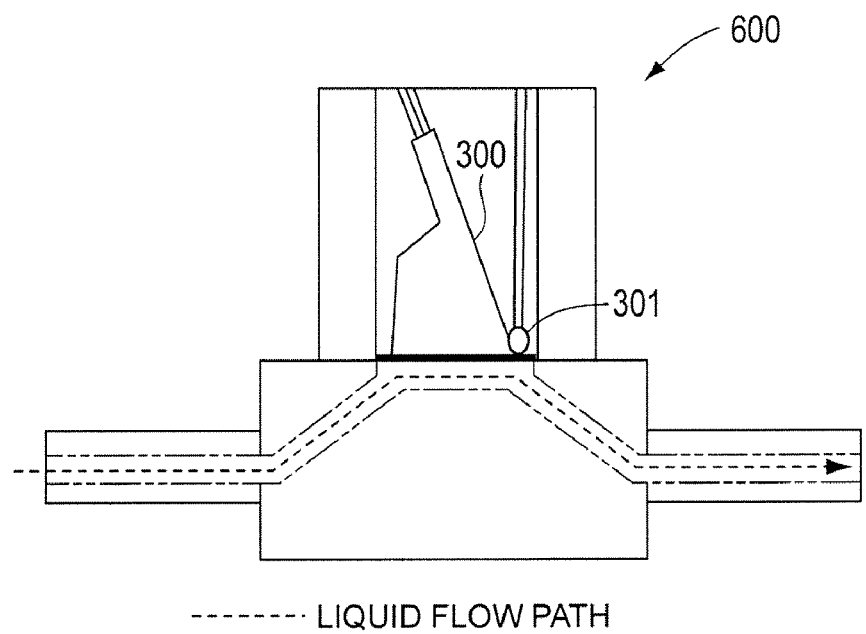
FIG. 6*a* illustrates an optical sensor coupled to an optical fluidic cell (OFC) according to an embodiment of the present invention.

Referring to FIGS. 6*a-d* the optical sensor 300 of the present invention is packaged into an OFC or OFM designed to withstand high liquid flow rates and high pressure and to be compatible with all liquid chemicals including slurries, acids, bases, solvents, caustics, biological materials and ultrahigh purity chemicals. Referring to FIG. 6*a* in the preferred embodiment of the present invention and in the case of a flowing liquid, the present invention utilizes a geometry that enhances mixing of solutions, mixtures, slurries, etc. at the optical window 147. This aspect of the present invention overcomes any static hydrodynamic boundary layer that may occur at or near the sensor surface therefore improving resolution and accuracy of the concentration measurement.

Referring to FIG. 6*a*, in one embodiment of the present invention, an optical fluidic cell (OFC) 600 provides for the sampling interface between the optical sensor 300 and the liquid under analysis. The OFC 600 materials of construction are compatible with acidic, basic, corrosive, solvents, ultrahigh purity, biological and biochemical applications. The OFC 600 includes a thermistor 301 to measure the liquid temperature. In the preferred embodiment of the present invention, temperature measurement relative to the internal housing of the sensor head 300 is input into a firmware algorithm as a temperature compensation feature (see FIG. 16).

Figure 6B:
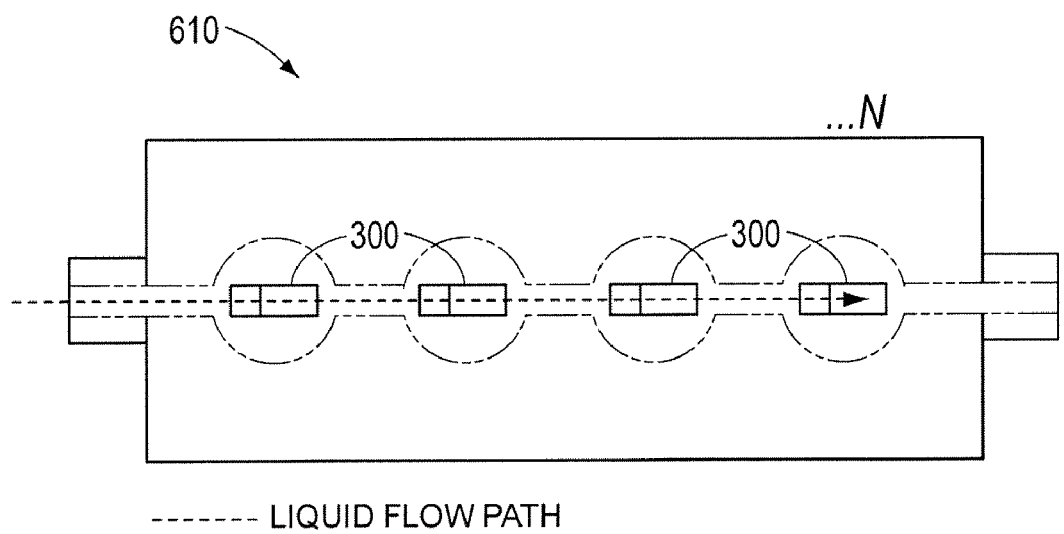
FIG. 6*b* illustrates an inline optical-fluidic manifold (OFM) including multiple optical sensors according to an embodiment of the present invention.

Referring to FIG. 6*b*, in another embodiment of the present invention, an optical fluidic manifold (OFM) 610 is shown. In this embodiment, 1, 2, 3 . . . N optical sensors 300 can be used simultaneously. Each optical sensor 300 can be calibrated (see FIG. 15) to a specific chemical species in a chemical mixture or solution. This method increase resolution for analysis of concentration of each chemical species.

Figure 6C:
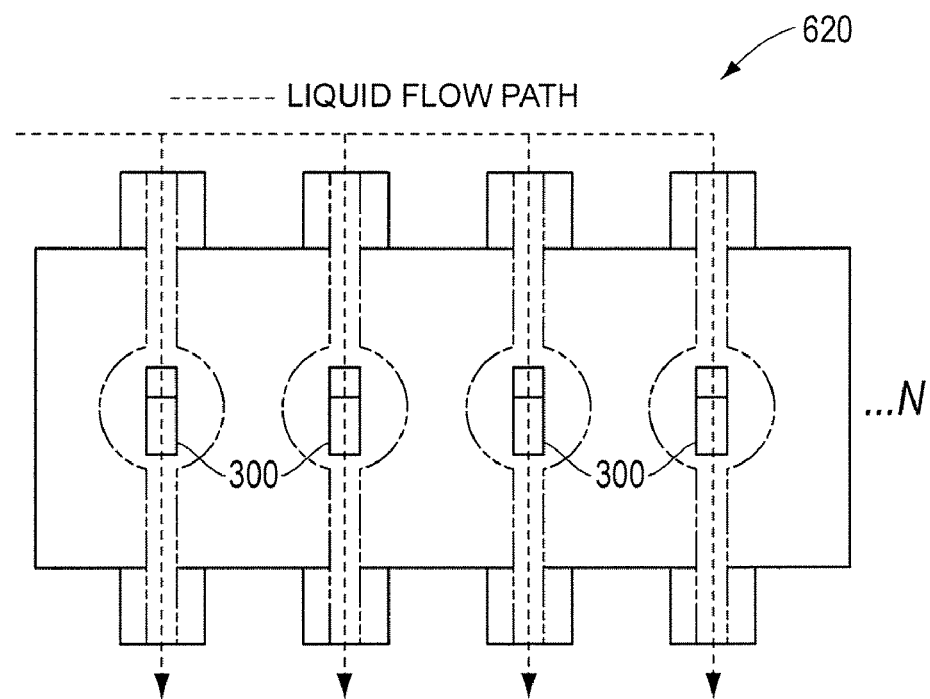
FIG. 6*c* illustrates a parallel inline optical-fluidic manifold (OFM) including multiple optical sensors according to an embodiment of the present invention.

In another embodiment shown in FIG. 6*c*, an OFM 620 may be modified to separate a single fluid stream into 1, 2, 3 . . . N parallel fluid streams.

Figure 6D:
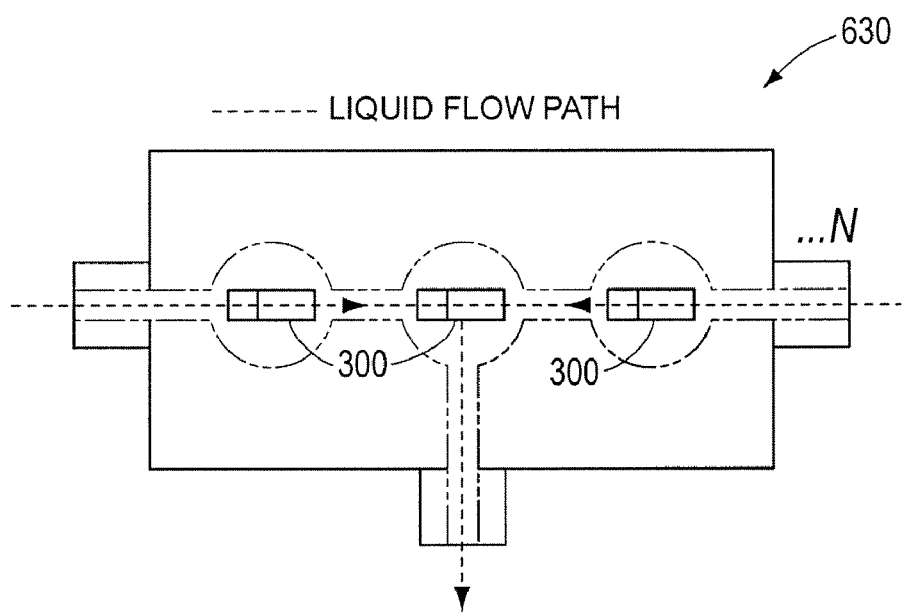
FIG. 6*d* illustrates a dual input single output optical-fluidic manifold (OFM) including multiple optical sensors according to an embodiment of the present invention.

Referring to FIG. 6*d*, in yet another embodiment 1, 2, 3 . . . N unique fluid streams can be input into an OFM 630. This arrangement may provide measurement of several chemical species in a liquid simultaneously or measure several distinct species in several distinct liquids simultaneously. These types of measurements are enabled by the calibration method (see FIG. 15).

The optical sensor 300 of the present invention can be used in conjunction with an OFC or OFM to increase the number of distinct types of chemical species to be analyzed and the sensitivity and dynamic range of the analysis system.

A sampling interface 514 of the optical sub-system 510 depends primarily upon the type of OFC 600 or OFM 610, 620, 630 used in the optical sub-system 510. Thus, direct contact, parallel flow, and static configurations are suitable OFC or OFM types. For example, the optical sensor 300 of the optical sub-system 510 can be manually introduced into the sample to make contact along a surface or other region of the optical sensor 300. Other sampling interfaces include fluidics, wherein the liquid sample is allowed to run over the optical sensor 300. In one use of the invention, the optical sub-system 510 is used in-situ and the electronic sub-system 520 is held at distance from the optical sub-system 510.

Referring to FIG. 5, communications interface 550 is provided to allow the optical sub-system 510 and electronic sub-system 520 to communicate via a wide array of communications formats. For example, communications interface 550 may comprise a plurality of signal paths or wires connecting the optical sub-system 510 to the electronic sub-system 520 which define physical signal pathways. Fiber optic cabling, twisted pair wiring, network, coax or other physical connections mediums may be used. Also, a communications protocol such as serial and/or parallel data transfers between the optical sub-system 510 and the electronic sub-system 520 may be employed. Likewise, communications interface 550 may take the form of a wireless communications system between the two sub-systems 510, 520 including radio frequency, infrared, satellite or other signal frequencies. Other communications interfaces 550 include point-to-point, on demand, secured transmissions or other custom communications protocol.

On the electronic sub-system 520 side, various functional features are provided and operationally coupled to each other. A source of power 521 is provided to activate and run the various active components of the electronic sub-system 520. Power source 521 can be solar, battery driven, alternating current, direct current, a generator or a remote power source, according to the invention.

An interface 522 gives the user input and functional control of the electronic sub-system 520 depending on the specific application of the analysis system 500. A keyboard, control pad, mouse, touch screen or other forms of control and input may form part of the interface 522. Likewise, the interface 522 may be implemented as a remote control subassembly of the electronic sub-system 520 which is operationally coupled to the analysis system 500 for remote use and operation. In yet another contemplated embodiment, the interface 522 comprises a switch or button which the user activates in order to command sensor functions.

Software/firmware 523 may be maintained on the electronic sub-system 520 to control the various sensors functions and processes according to the specific sensor application. In one embodiment, the software/firmware 523 is controlled by the user interface 522 allowing the user to view and display data results via display 525 and/or otherwise manipulate the sample related data as obtained by the optical sub-system 510.

For example, the user can use interface 522, software/firmware 523, and display 525 to determine when the sample of interest is detected by the optical sub-system 510. The data can be manipulated, graphed or otherwise analyzed depending on software/firmware 523 features. A help system may also be included in the software/firmware 523 to assist the user with various analysis system 500 features. The software/firmware 523 may be used to store, retrieve or transmit data and/or commands to the sensor or a remote processing system according to the invention.

Also shown is a storage area 524 that can be a hard disk, floppy disk or other magnetic means of storage or a chip-based storage device such as DRAM, EEPROM, flash memory, ROM or other similar components. Storage area 524 provides a space where sample related data, test history, calibration information or other similar data can be stored.

A display 525 may be included and operationally coupled to the various components of the electronic sub-system 520. In an embodiment of the analysis system 500, display 525 comprises one or more LEDs which are actuated at times when the optical sub-system 510 detects the presence of the particular sample of interest. In other embodiments, display 525 comprises a liquid crystal display (LDC), a monitor or CRT which provides alpha-numeric output relating to the sample of interest. Other displays 525 include hard copy, digital or analog signal outputs, audio alarm, synthetic voice, pager or projection among others.

Also shown is an electronic circuit 526 that includes a signal processor 527 in the electronic sub-system side 520 of the analysis system 500 which converts, processes, assembles and otherwise manipulates the data received from the optical sub-system 510. In one embodiment, the optical sub-system 510 generates a digital bitstream data output related to the sample of interest which is relayed via communications interface 550 to the electronic sub-system 520 and received by the signal processor 527 for further analysis. The data may be the output of an analog-digital converter which may be integrally molded on the optical sensor 300 or mounted externally.

In another embodiment, the output from the optical sub-system 510 is a modulated carrier that is transmitted to the signal processor 527 of the electronic circuit 526 via a wireless communications mode of communications interface 550.

For example, an RF transmitter can be incorporated in the optical sub-system 510 as part of communications interface 550 and used to modulate an airborne signal which is received by the communications interface 550 side of the electronic sub-system 520 and transferred to the signal processor 527 for demodulation and further analysis.

Figure 7:
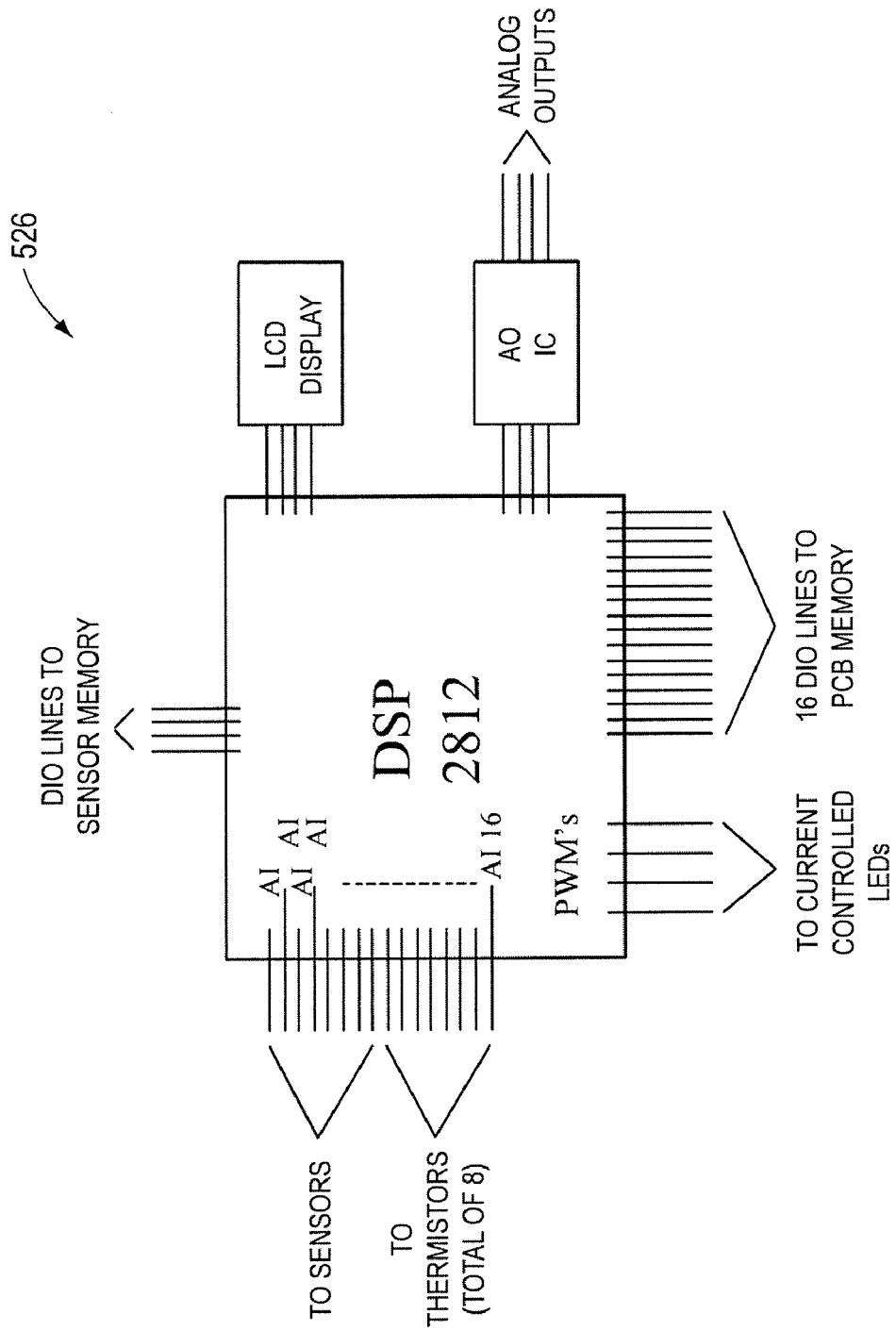
FIG. 7 illustrates a digital signal processor (DSP) based electronic drive circuit according to an embodiment of the present invention.

FIG. 7 illustrates an electronic circuit 526 that incorporates a digital signal processor (DSP) as the signal processor 527. The DSP chip includes firmware and software inputs and data outputs and may be of a type readily available in the industry.

Figure 8A:
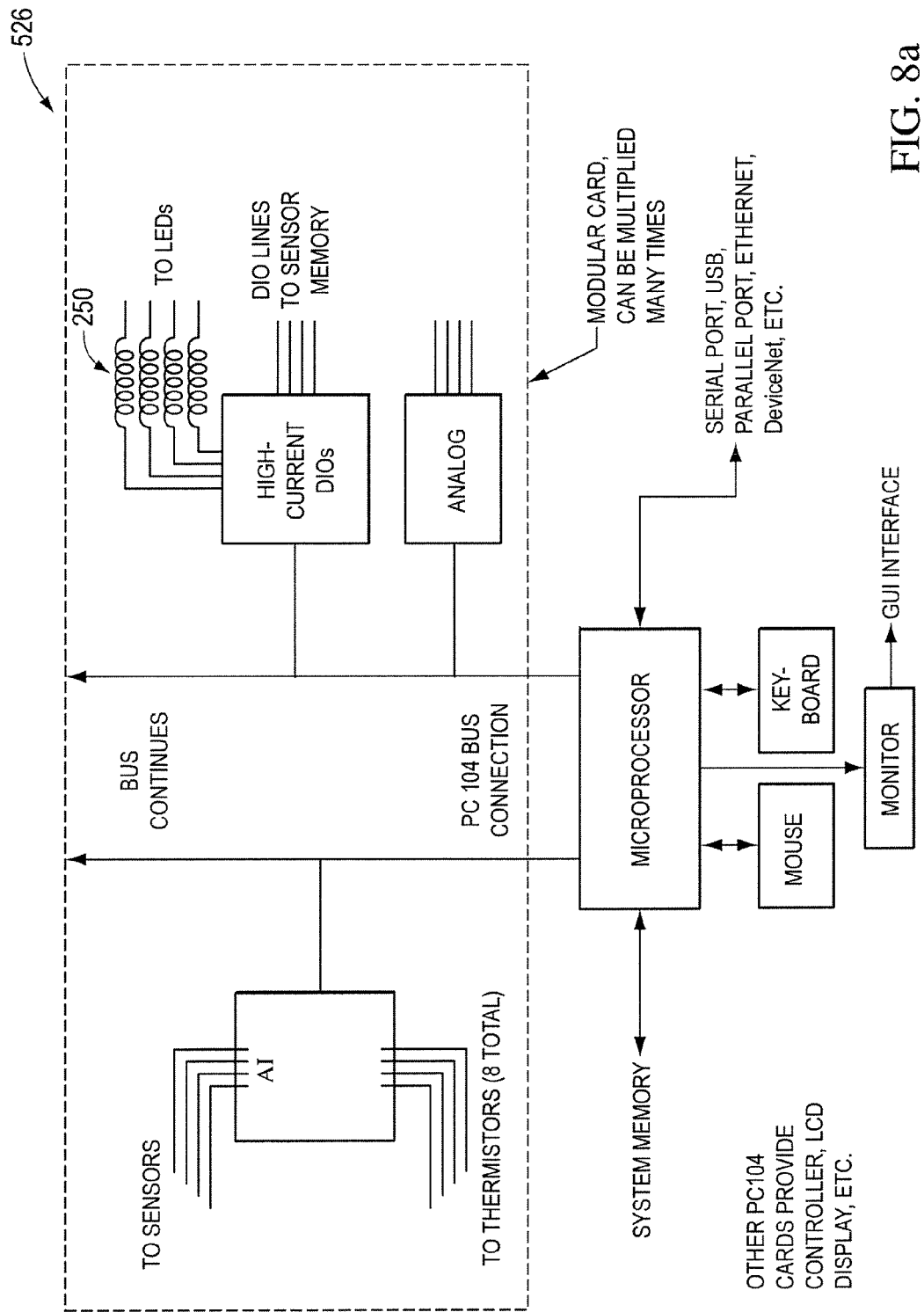
FIG. 8*a* illustrates a PC104 based electronic circuit according to an embodiment of the present invention.

FIG. 8a illustrates an electronic circuit 526 that includes a PC104-based embedded computing platform on a modular card that connects via a PC104 bus connection to a microprocessor that serves as the signal processor 527. Also a microcontroller, microprocessor or other high scale integrated circuit can be used as the signal processor 527 to analyze the incoming data from the optical sub-system 510. Other options include a data analyzer, calculator or application specific integrated circuit (ASIC).

Figure 8B:
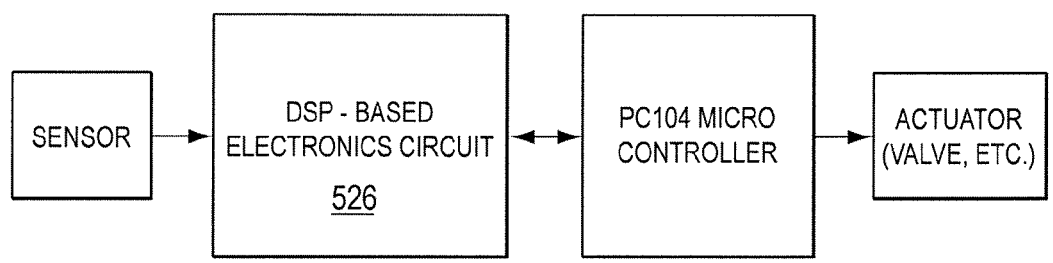
FIG. 8*b* illustrates a digital signal processor (DSP) based electronic drive circuit interfaced to a PC104 based microcontroller according to an embodiment of the present invention.
Figure 8C:
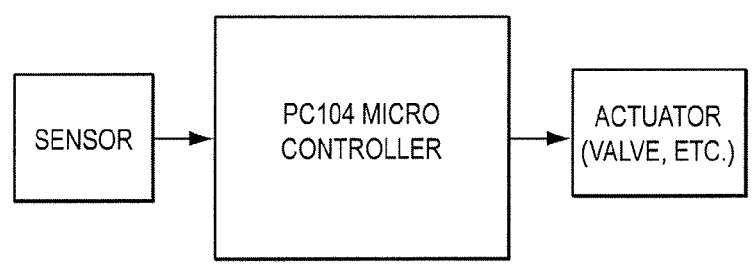
FIG. 8*c* illustrates a PC104 based electronic circuit for use as a sensor electronic circuit and a controller electronic circuit according to an embodiment of the present invention.

Referring to FIG. 8b, in another embodiment, the DSP-based electronic circuit 526 is interfaced to a PC104-based microcontroller, which is in turn interfaced to an actuator (valve, pump, etc.) for closed loop control of liquid processes. Referring to FIG. 8c, in another embodiment, the PC104-based electronic circuit 526 is used both as the sensor electronic circuit and as the controller electronic circuit for closed-loop control applications.

IoR measurements are sensitive to the temperature of the liquid under analysis. Furthermore, temperature changes of the optical sensor housing will lead to changes in optical properties of the photo detector 110 and other optical components, which lead to "false" readings that adversely affect concentration measurements. In order for the present invention to be fully automated and highly accurate, temperatures of both the optical sensor housing and the fluid under analysis are closely monitored and temperature changes are compensated for.

Figure 9A:
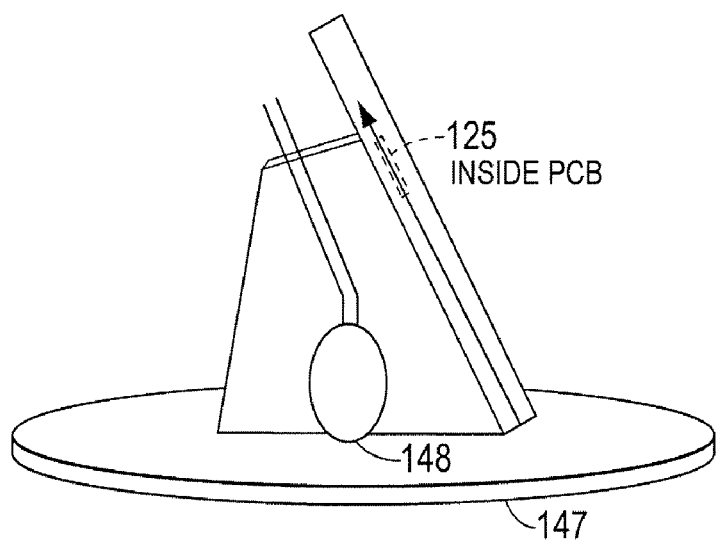
FIG. 9*a* illustrates a dual temperature compensation apparatus according to an embodiment of the present invention.

FIG. 9a illustrates an apparatus utilized in a Two Coefficient Thermal Compensation method according to embodiments of the present invention. The apparatus consists of a thermistor 125 placed inside the optical sensor housing and a second thermistor 148 placed on the backside of the optical window 147. The thermistor 125 is used to monitor the temperature of the optical sensor housing. The second thermistor 148 is used to monitor the temperature of the fluid under analysis.

Figure 9B:
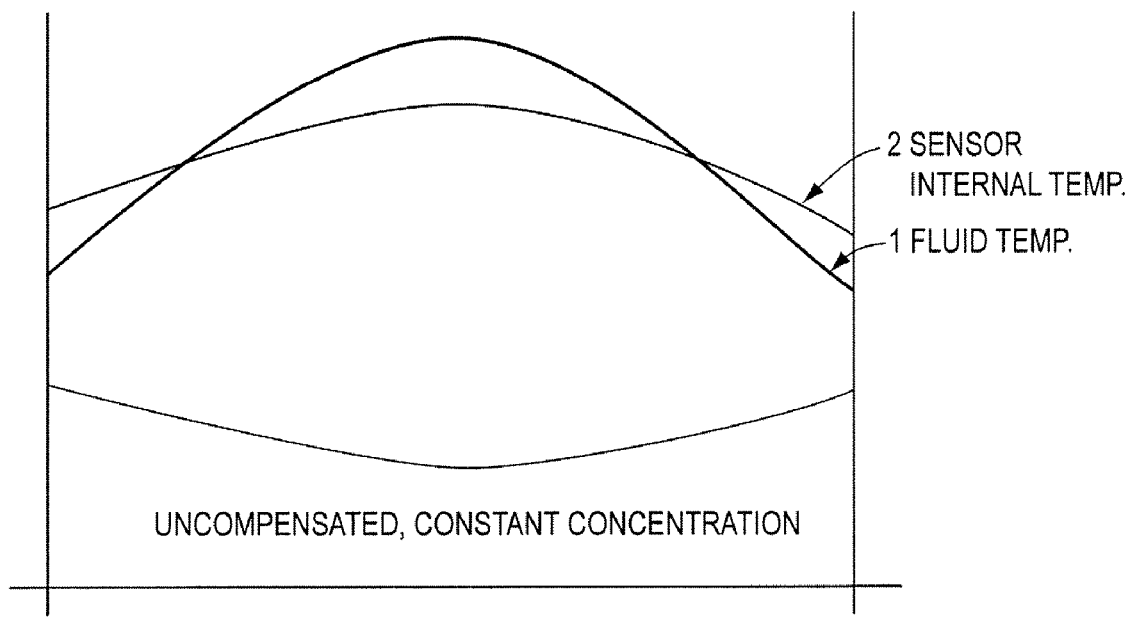
FIG. 9*b* illustrates temperature readout from two thermistors of the dual temperature compensation apparatus and uncompensated concentration behavior according to an embodiment of the present invention.
Figure 9C:
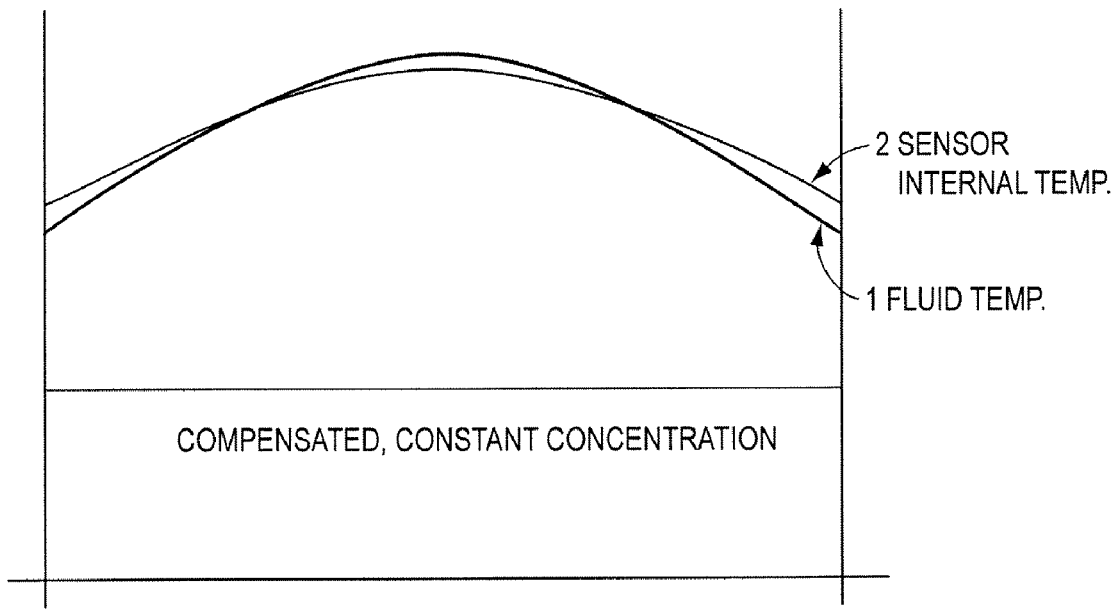
FIG. 9*c* illustrates compensated concentration behavior according to an embodiment of the present invention.

Referring to FIG. 9b, temperature is plotted as a function of time for the thermistors 125 and 148. The uncompensated concentration of the liquid under analysis varies as temperature changes, even though the actual concentration is constant. Referring to FIG. 9c, the temperature compensated concentration is flat, matching the actual concentration.

Embodiments of the present invention utilize a three-stage method for calibration, measurement, and conversion of IoR to liquid chemical concentration. For example, in stage 1 of the method, the calibration method shown in FIG. 10 may be used to translate a pixel position generated by a Mass Moment (MM) algorithm into a measured IoR that is uncompensated for temperature. The calibration method may be based on calibration points obtained at 25 degrees Celsius.

In stage 2, a temperature compensated IoR may be calculated utilizing a linear equation using a sensor temperature measured by the thermistor 125 in the optical sensor 300 and a known fluid temperature measured by a thermistor 148 placed on the backside of the optical window 147. See equation 2 below.

Figure 11:
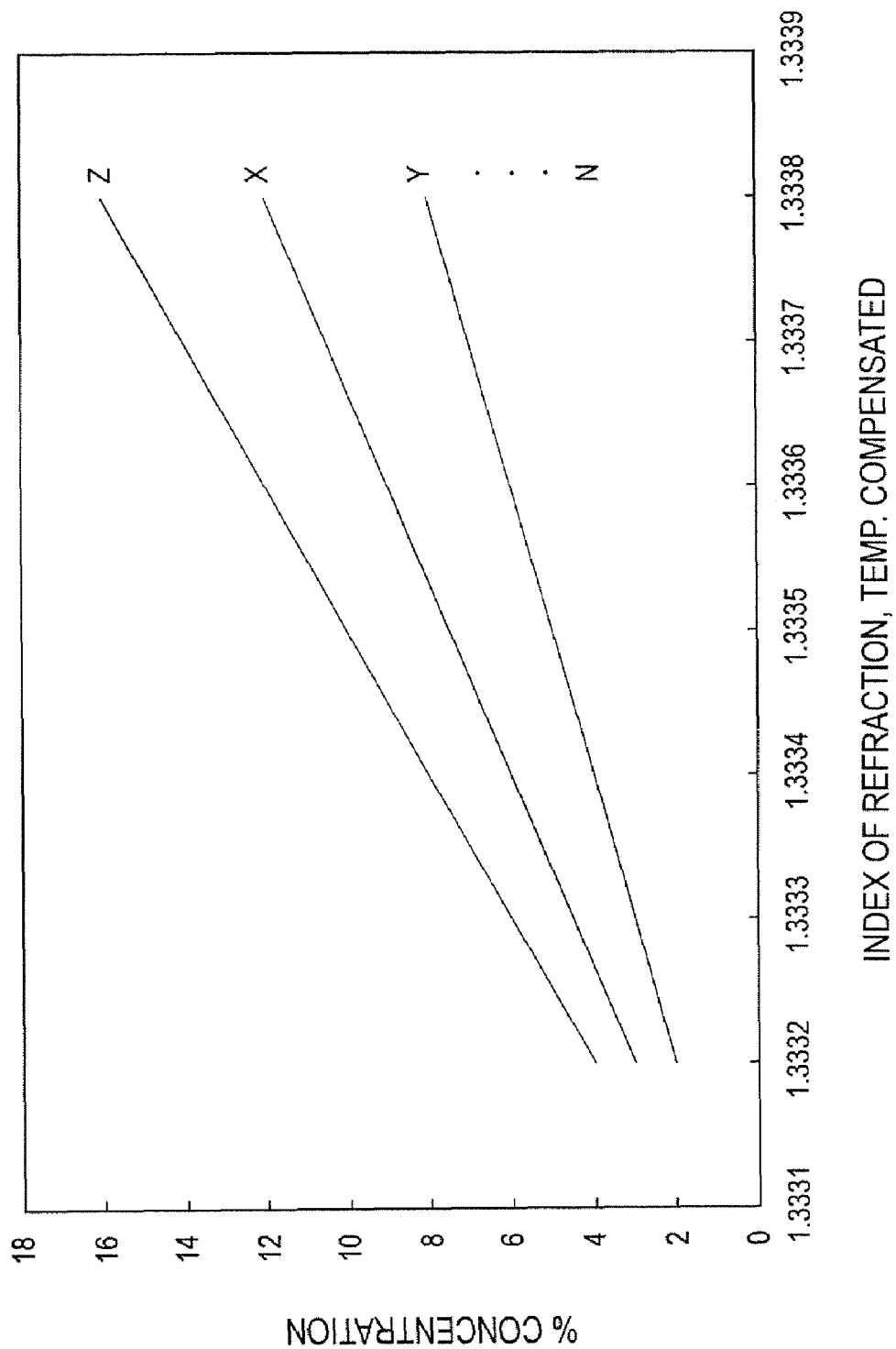
FIG. 11 illustrates concentration versus temperature compensated Index of Refraction according to an embodiment of the present invention.

Most liquids have a linear relationship between temperature compensated Index of Refraction ($IoR_{TC}$) and concentration; therefore, two points on a line are often enough for a conversion. Furthermore, these two points will be the same for all sensors, so that the table (or curve) for a given chemical only has to be generated once. Referring to FIG. 11, concentration versus $IoR_{TC}$ shows a linear relationships between concentrations and $IoR_{TC}$ for three chemicals; X, Y and Z. The slope of the line ($IoR_{TC}$=slope*concentration+ Co) is an indication of the relative chemical concentration.

In stage 2, the signal processor 527 determines $IoR_{TC}$ using a sensor temperature measured by the thermistor 125 in the optical sensor 300, a known fluid temperature measured by the thermistor(s) 148, the measured Index of Refraction as a function of time, and the following equation (see FIG. 12*a-d*):

$$IoR_{TC} = IoR - A(T_f - 20) + B(T_s - 20);$$

$$A \approx 1.3e-04;$$

$$B \approx 0.3e-04 \quad (2)$$

Where $IoR_{TC}$ is the temperature compensated Index of Refraction, IoR is the measured Index of Refraction, $T_f$ is the known temperature of the fluid, $T_s$ is the temperature of the sensor, and A and B are constants.

Referring to FIG. 11, in stage 3 of the calibration method, the signal processor 527 utilizes either a curve or lookup table to translate $IoR_{TC}$ to liquid concentration.

In an alternative embodiment of the present invention, equation (3) is used in a firmware algorithm to perform temperature compensation of the concentration measurement as follows:

$$C_{compensated} = C_{uncompensated} + A(T_{148} - T_{calibration}) + B(T_{125} - T_{148}) \quad (3)$$

Where $T_{148}$ is the temperature reading from thermistor 148, $T_{125}$ is the temperature reading from thermistor 125, and A and B are constants determined from initialization and calibration. Note that equation (3) is a generalization of equation (2) above. Furthermore, equation (3) is written alternatively in terms of "chemical concentration," where as equation (2) is written in terms of IoR.

Figure 9D:
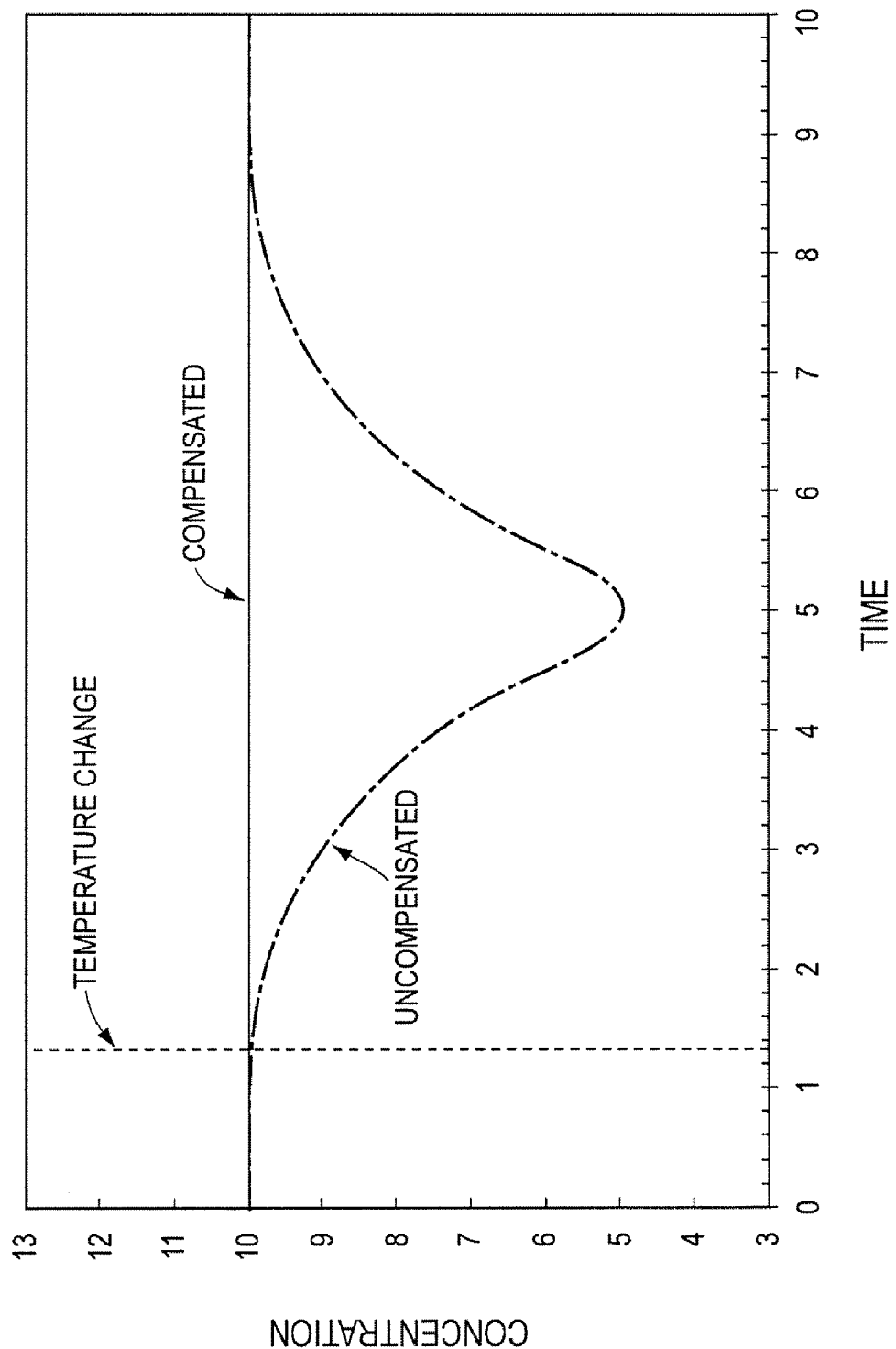
FIG. 9*d* illustrates a lead/lag thermal compensation according to an embodiment of the present invention.

FIG. 9*d* illustrates temperature compensation for an alternative embodiment of the present invention. Referring to FIG. 9*d*, the effect of transient temperature fluctuations, which occur on small time scales (seconds), on a concentration measurement are shown. In the preferred embodiment of the present invention the effect of temperature fluctuations on concentration are removed as shown by the flat second curve of FIG. 9*d*. In the preferred embodiment of the present invention, the effects of temperature fluctuations are removed by implementing a lead/lag compensation filtering algorithm in the electronics circuit. In an alternative embodiment of the present invention non-linear terms are included in equations (2) and (3). These non-linear terms are used to compensate for the effect of temperature fluctuations on concentration.

A key innovation of the present invention is that by eliminating sensor-to-sensor variations in IoR, the three-stage calibration method becomes sensor independent. The signal processor 527 may display the calculated concentration using, for example, display 525, a graphical user interface (GUI) or an LCD display.

Figure 13A:
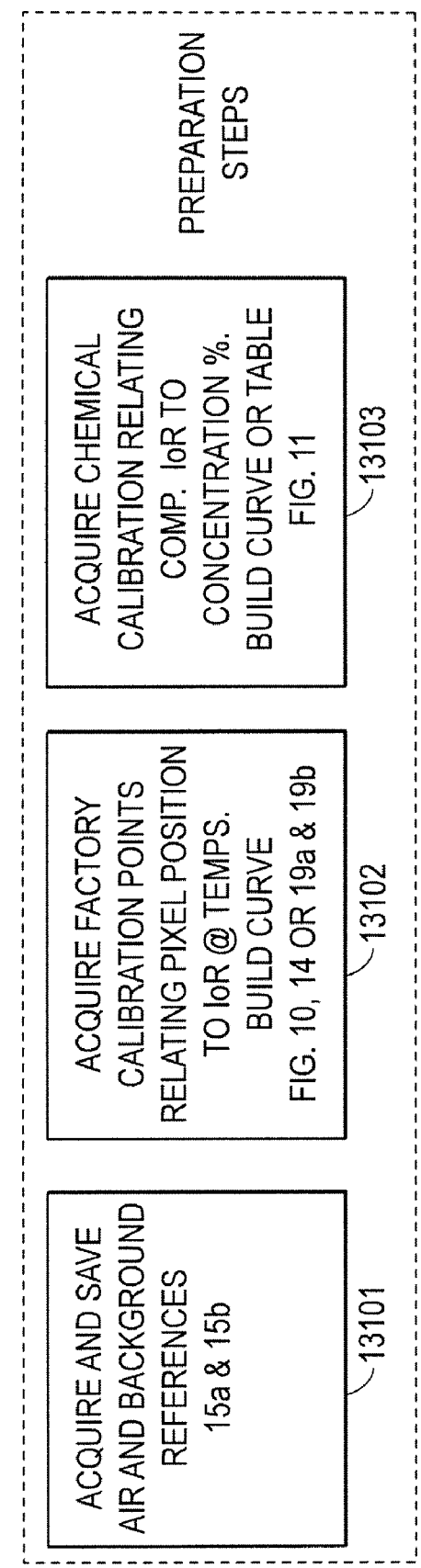
FIG. 13a illustrates a flow chart diagram of a method of calibration using an algorithm according to an embodiment of the present invention.
Figure 13B:
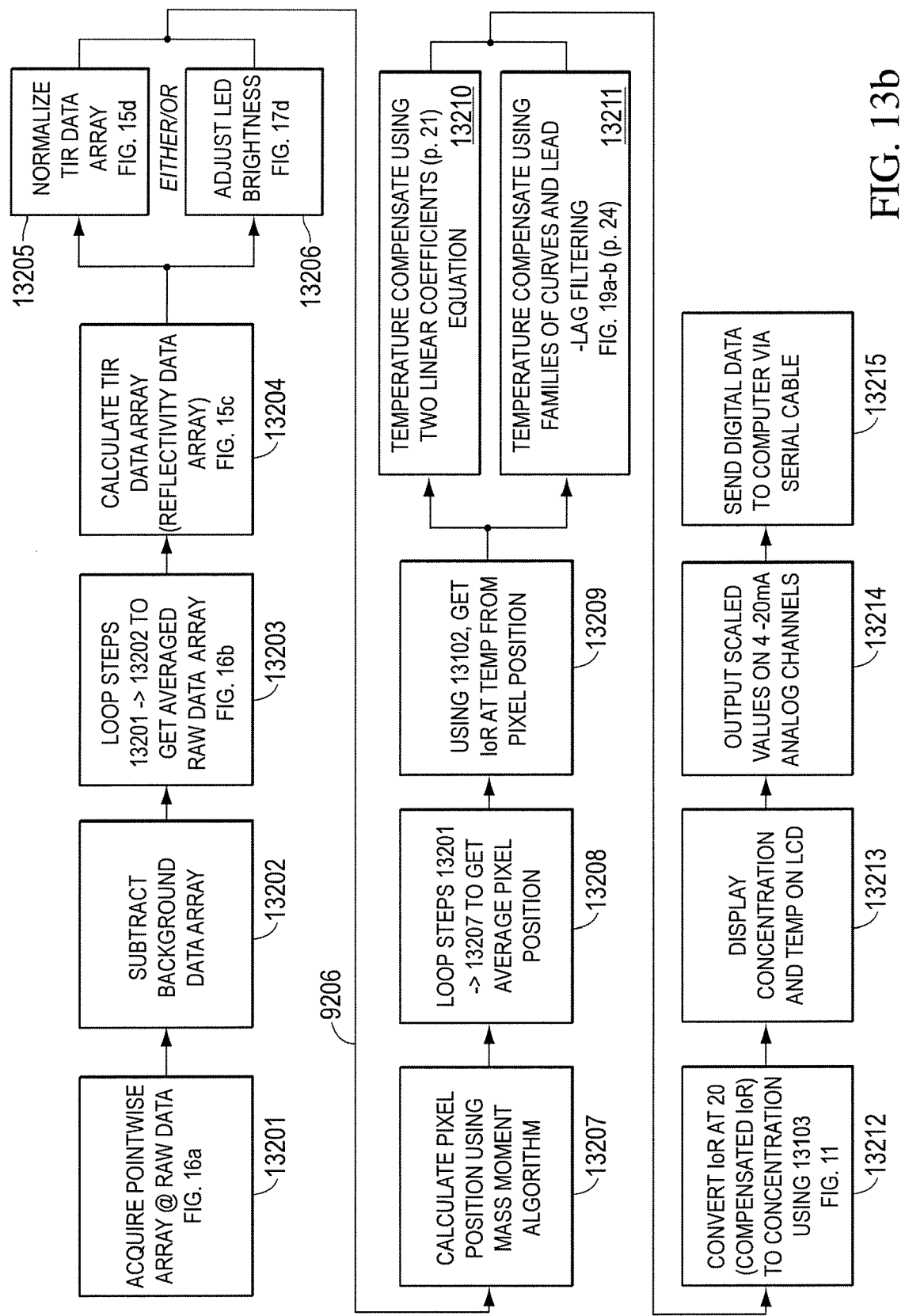
FIG. 13b illustrates a flow chart diagram of a method of measuring concentration in a liquid chemical using an algorithm according to an embodiment of the present invention.

FIGS. 13*a* and 13*b* illustrate flow chart diagrams of a method of measuring the concentration of a known chemical X in a liquid using an algorithm according to an embodiment of the present invention. FIG. 13*a* illustrates the preparation steps of data acquisition and analysis necessary for the detailed data manipulation that is illustrated in the flow chart diagram of FIG. 13*b*. FIG. 13*a* represents steps of the method including acquisition of air and background reference data 13101, acquisition of factory calibration data 13102 and acquisition of temperature compensated IoR as related to chemical concentration 13103.

Referring to FIG. 3, FIG. 5, FIG. 13*a*, FIG. 15*a* and FIG. 15*b*, the signal processor 527 acquires 13101 a background noise data from the photodetector array 110 by turning off the light source 120 in the optical sensor 300 and reading out the pixel data. The signal processor 527 acquires 13101 an air reference data from the photodetector array 110 by making a measurement with air as the sample in contact with the optical sensor 300 and reading out the pixel data.

Figure 16A:
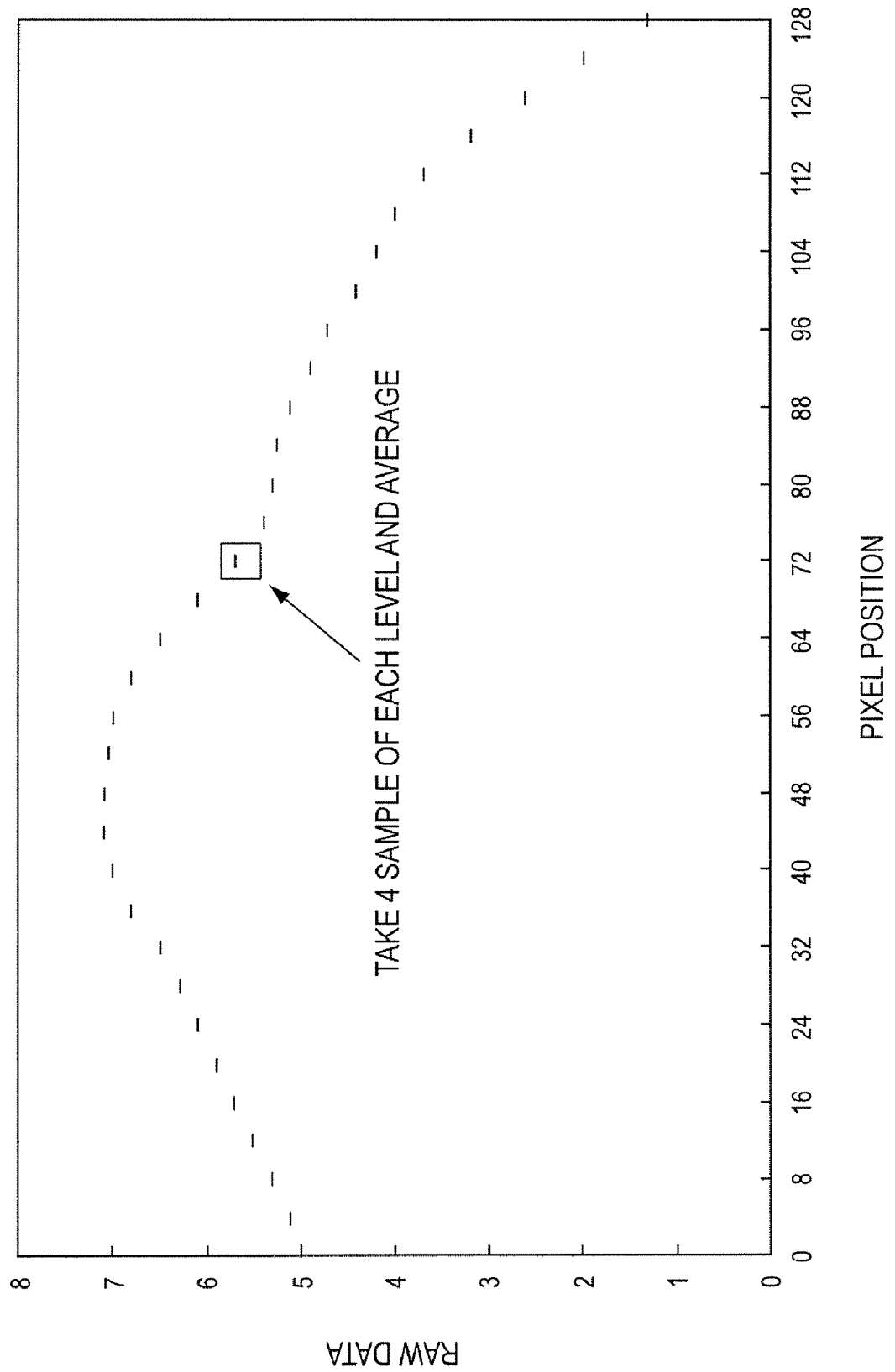
FIGS. 16a-c illustrate the three stages of signal processing and data averaging according to an embodiment of the present invention.
Figure 16B:
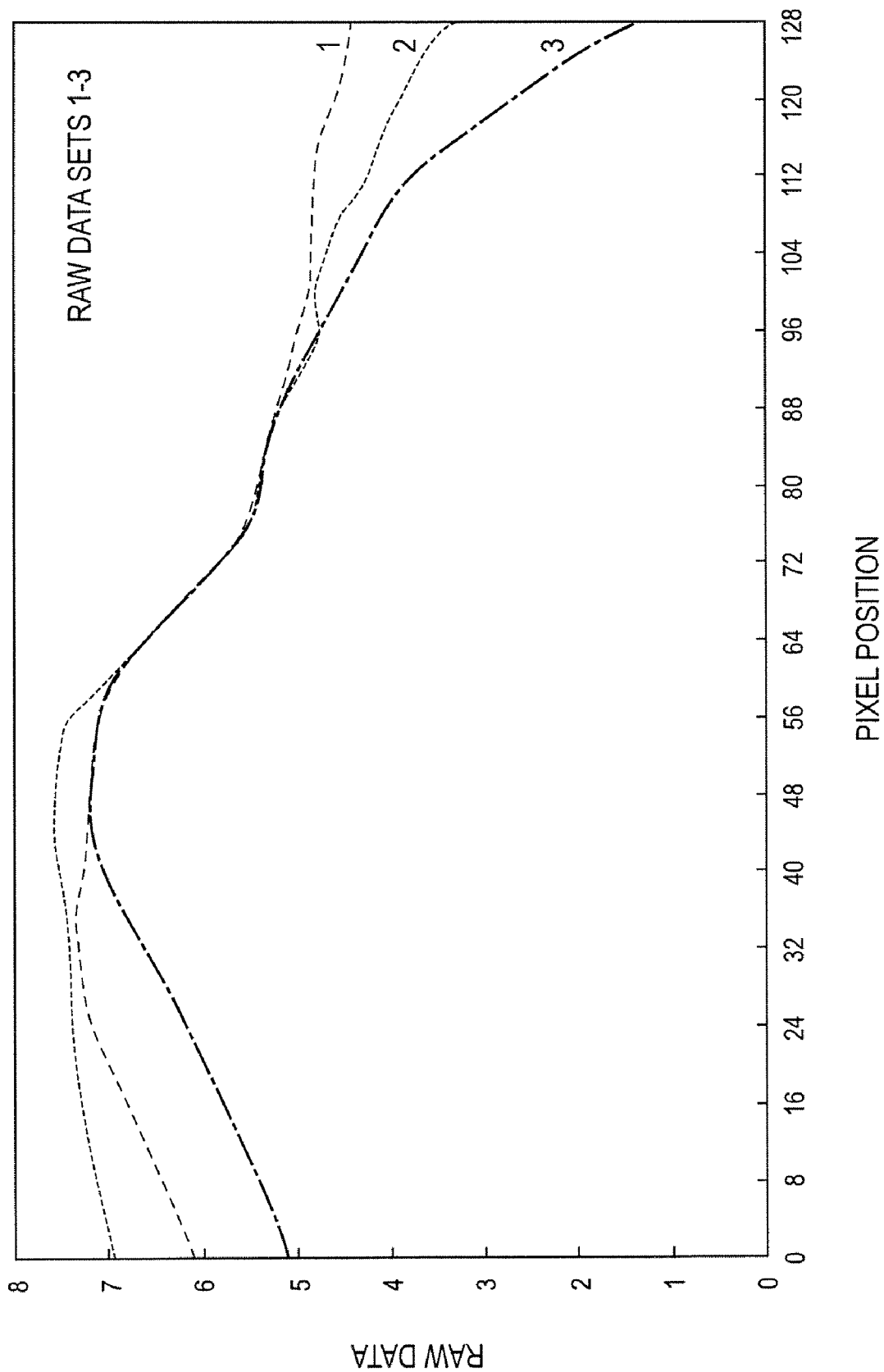

Referring to FIGS. 16*a* and 16*b*, the air reference data set and background noise data undergo two steps of averaging. First, for each pixel position of the photodetector 110, each channel reading may be averaged 4 times. This averaging requires taking multiple measurements of each pixel voltage during each data acquisition. Second, the next averaging step includes obtaining three data sets obtained by averaging according to step 1 and averaging the three complete data sets to obtain a single averaged data set.

Figure 14:
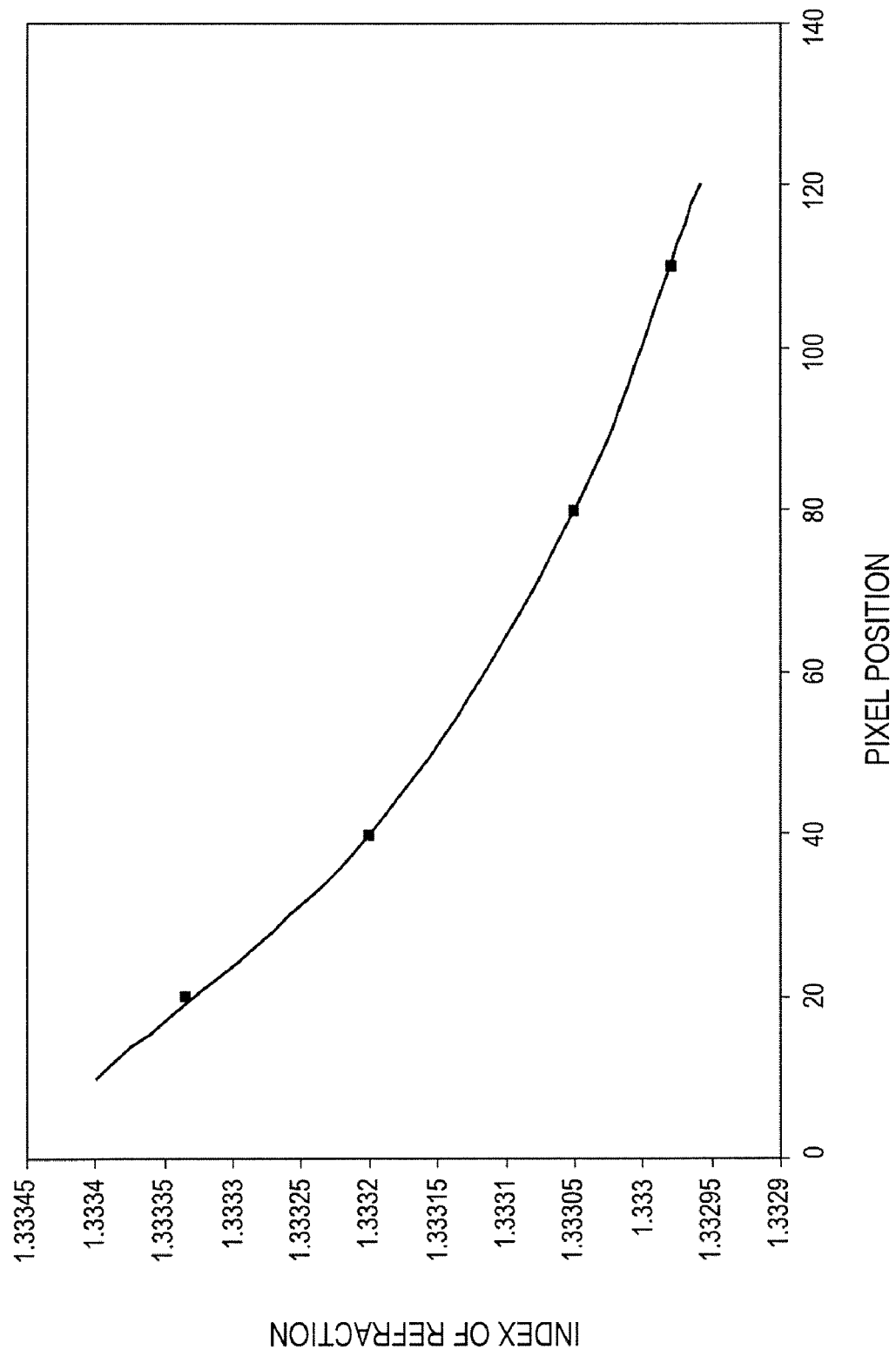
FIG. 14 illustrates calibration data according to an embodiment of the present invention.

Next, the signal processor 527 calibrates 13102 the Index of Refraction to pixel position using known concentrations of the known sample under test, chemical X. A polynomial least squares fit to a plurality of calibration points is used to generate the calibration curve of known chemical X (see FIG. 14). The calibration curve may be based on calibration points obtained at 25 degrees Celsius.

Figure 19A:
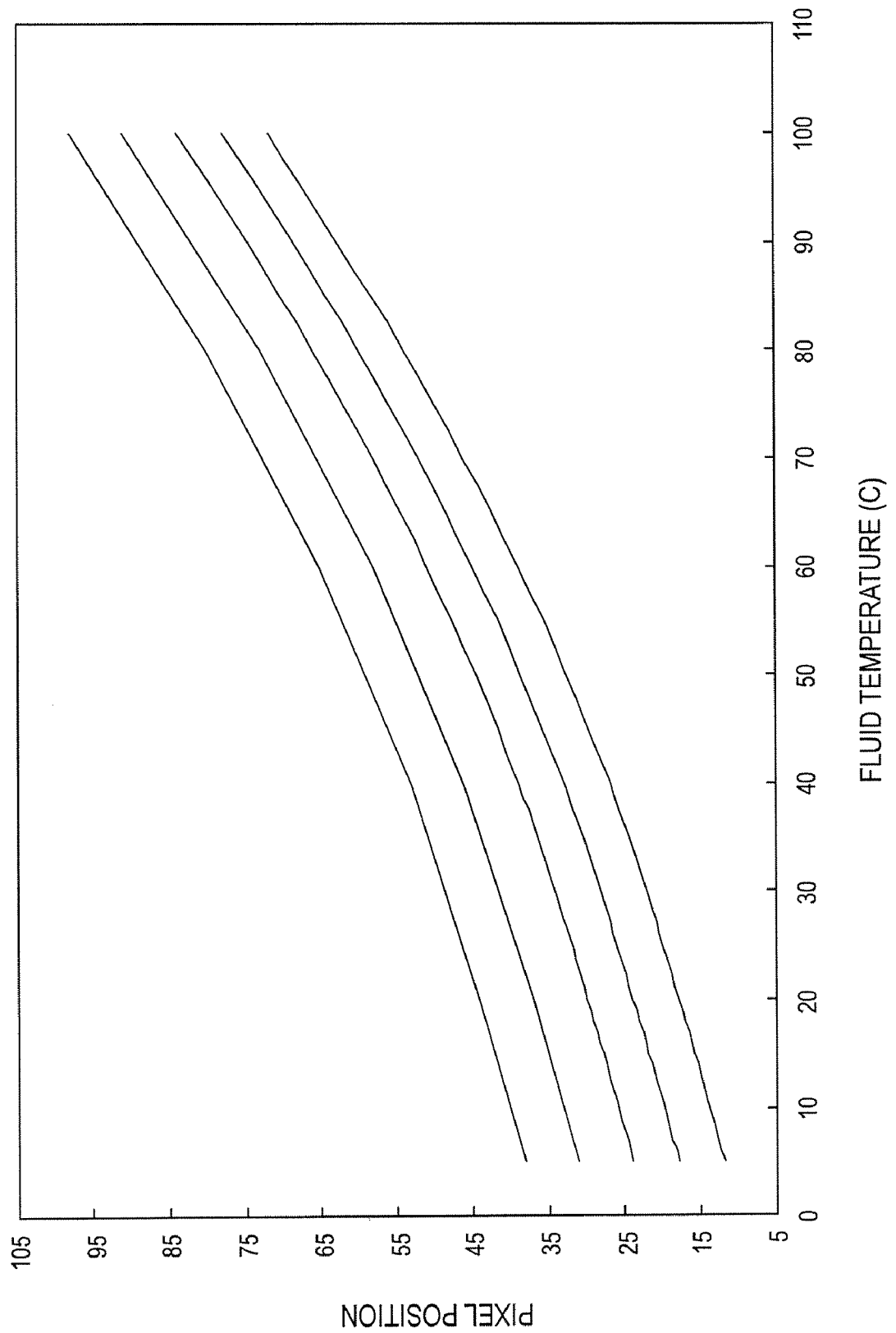
FIG. 19a illustrates pixel number versus fluid temperature data for various concentrations according to an embodiment of the present invention.
Figure 19B:
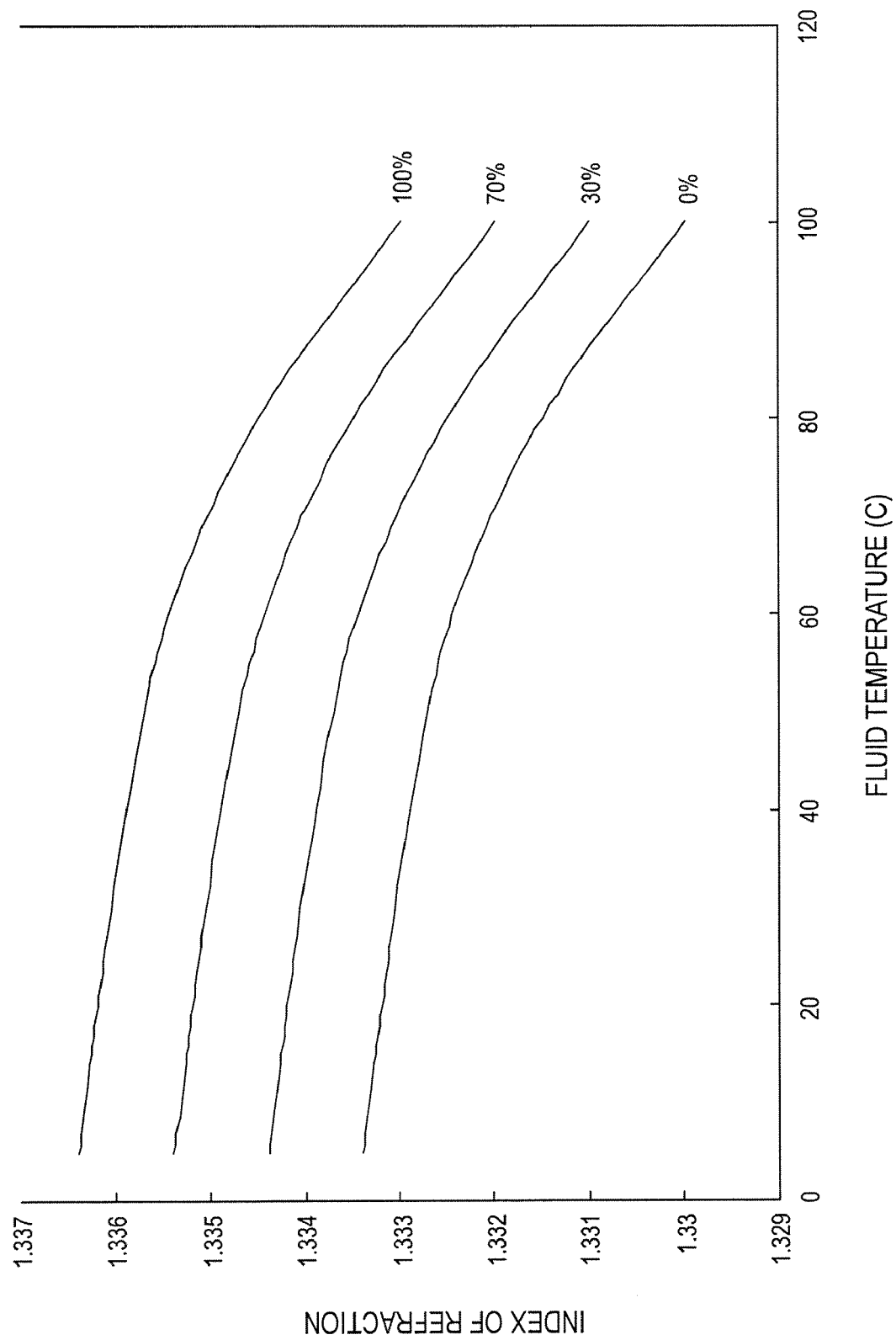
FIG. 19b illustrates Index of Refraction versus fluid temperature data for various concentrations according to an embodiment of the present invention.

Referring to FIGS. 19*a* and 19*b*, in the preferred embodiment of the present invention, calibration is performed over a range of fluid temperatures between 0° C. and 100° C. For the preferred embodiment of the present invention this method of calibration ensures accurate and real-time concentration measurements for any liquid chemical and ensures concentration analysis performance is nearly identical from sensor to sensor. In the preferred embodiment of the present invention, curves such as those shown in FIGS. 19*a* and 19*b* are included as lookup tables as part of the DSP or PC104 circuits (see FIGS. 7 and 8*a*, respectively).

Referring to FIG. 13*a* and FIG. 11, the next step is acquisition 13103 of chemical calibration data relating thermally compensated IoR to % chemical concentration.

Referring to FIG. 13*b*, the first stage of data signal analysis involves acquisition 13201 of the raw data signal. The first stage includes analog to digital (A/D) averaging as shown in FIG. 16*a*. The raw data versus pixel position is shown. For each pixel position of the photodetector 110, each channel reading may be averaged 4 times. The first stage requires taking multiple measurements of each pixel voltage during each raw data acquisition. This averaging helps deal with noise in the A/D conversion system of the DSP, or noise in the transmission wires, terminal junctions, etc.

Referring to FIG. 13b, the next step 13202 involves using the signal processor 527 to subtract the background noise data from the raw data and subtract the background noise data from the air reference data. This is shown in equations (4).

$$\text{Data}_{backgroundsubtracted} = \text{Rawdatasignal} - \text{Backgroundsignal}$$

$$\text{Data}_{airereferencesubtracted} = \text{Airereferencesignal} - \text{Backgroundsubtractednoisesignal} \quad (4)$$

Referring to FIGS. 13b and 16b, the next step 13203 involves "looping" steps 13201 and 13202 to obtain, for example, three averaged raw data sets and then taking the average of the three raw data sets to obtain a single averaged raw data set. In an alternate embodiment of the present invention, referring to FIG. 13b, "looping" and therefore averaging can be performed after calculation of the TIR data 13204. In this embodiment, step 13203 would occur after step 13204. This averaging stage addresses noise created by varying LED intensity, variations in integration time, or variations in photodiode array voltage response to light from data set to data set.

Figure 15A:
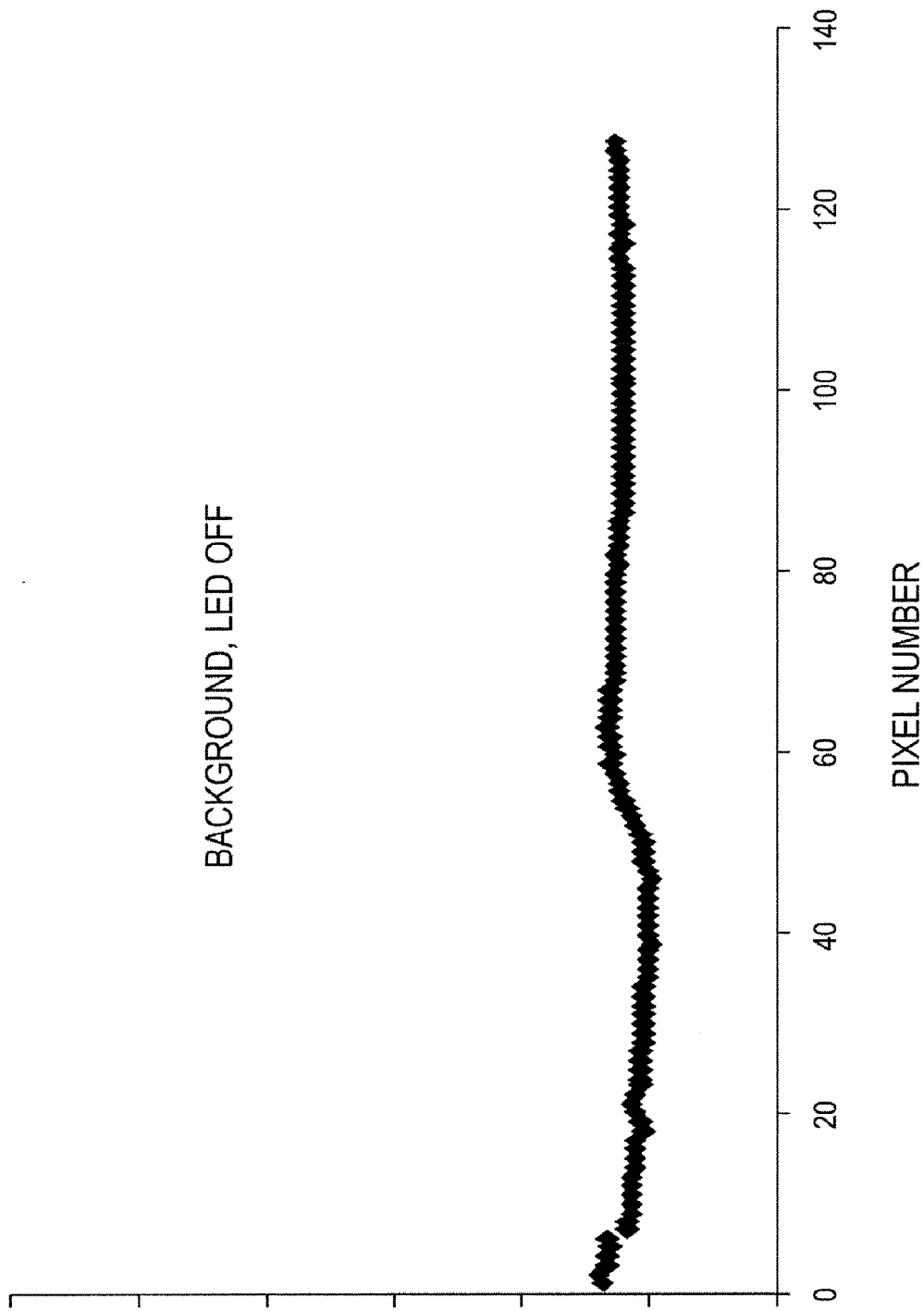
FIG. 15a illustrates the background noise data obtained from a photodetector array with a light source off according to an embodiment of the present invention.
Figure 15B:
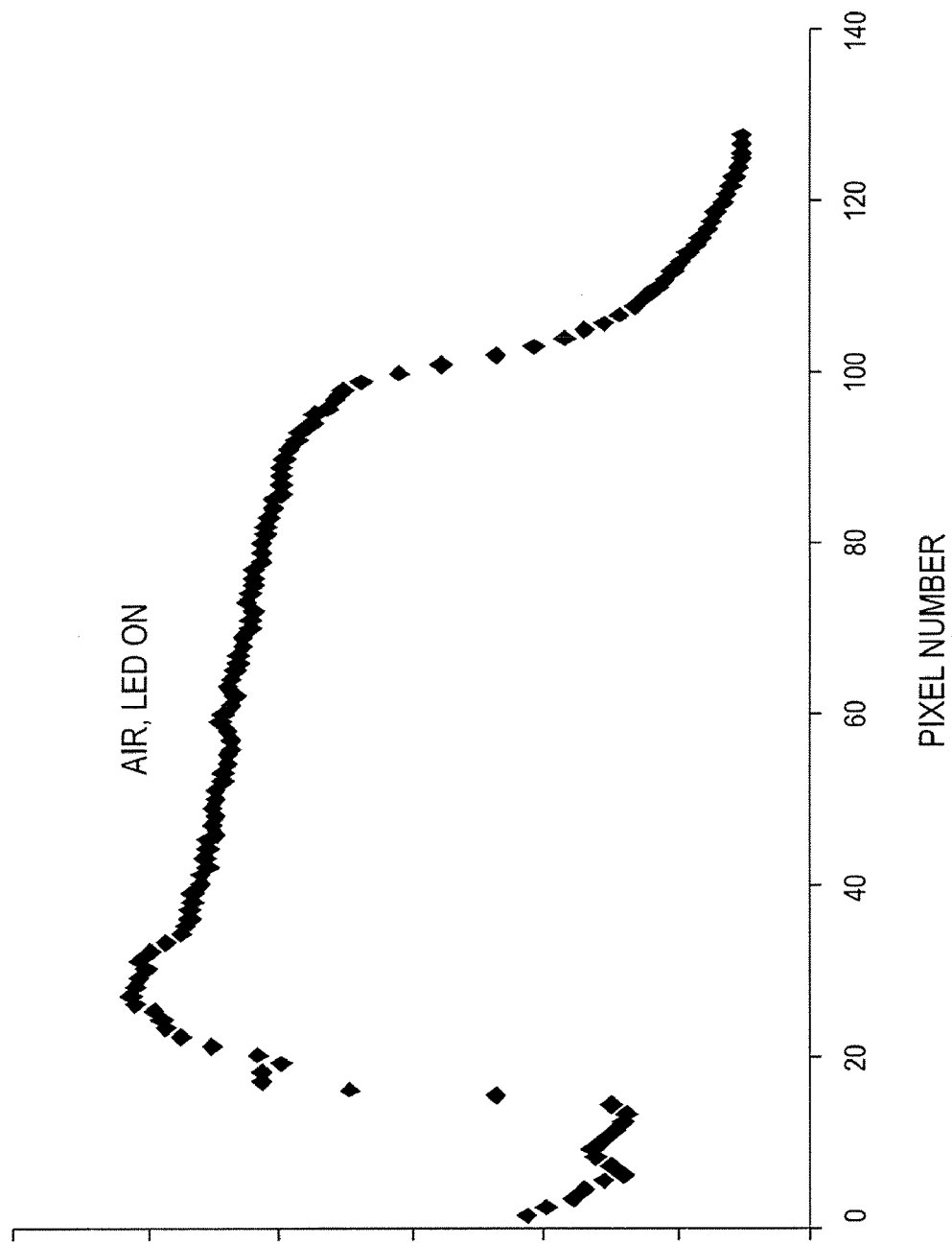
FIG. 15b illustrates the air reference data obtained from a photodetector array according to an embodiment of the present invention.
Figure 15C:
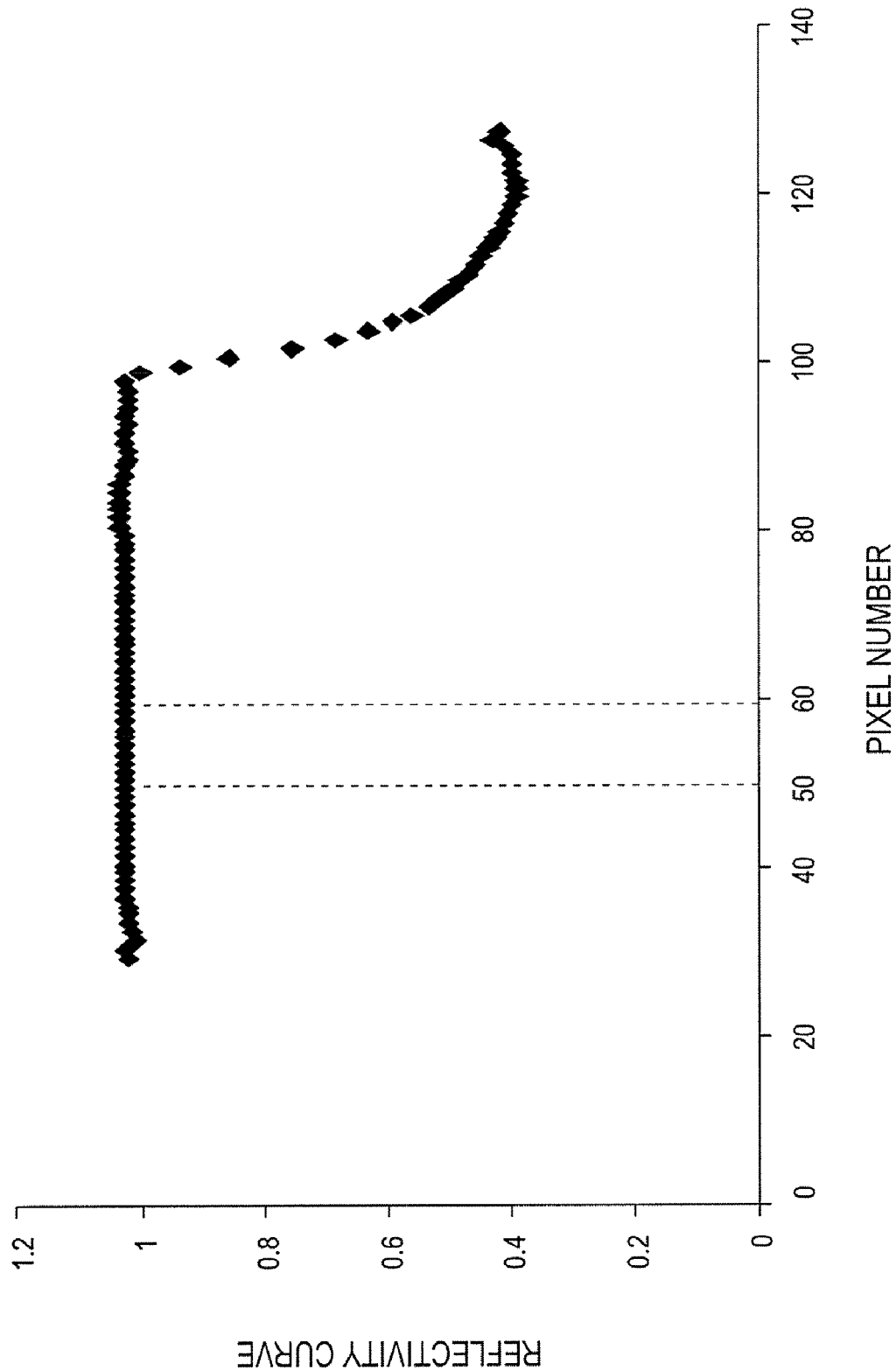
FIG. 15c illustrates the optical reflectivity data according to an embodiment of the present invention.
Figure 15D:
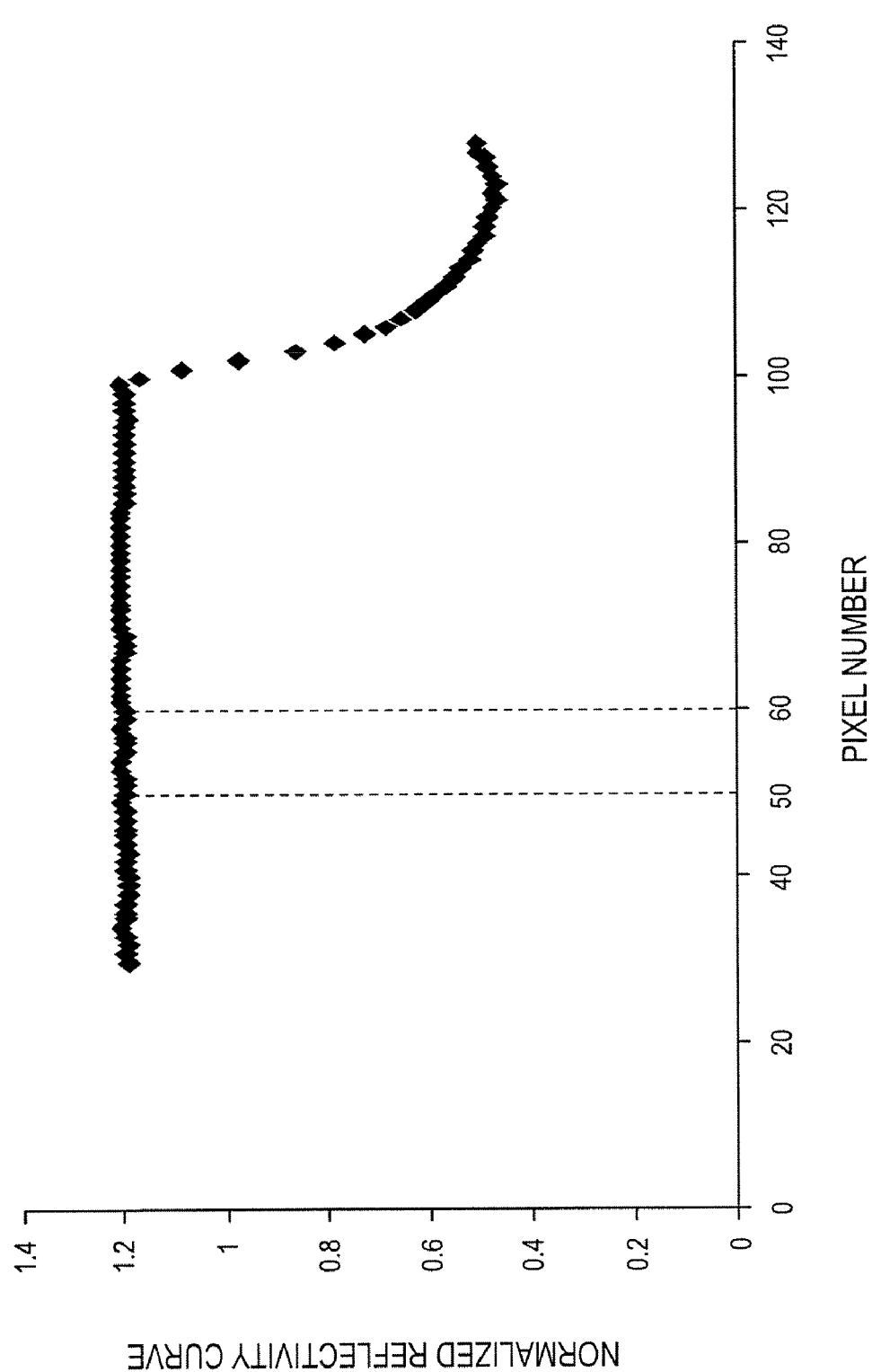
FIG. 15d illustrates the normalized reflectivity data according to an embodiment of the present invention.

Referring to FIGS. 13b and 15c, in the next step 13204 the signal processor 527 calculates a TIR data set (i.e., normalized and background corrected reflectivity data set) by dividing the result of subtraction of the background noise data set from the raw data set by the result of the subtraction of the background noise data set from the air reference data set according to the following equation (see FIG. 15c):

$$TIR = \frac{Data_{Backgroundedsubstracted}}{Data_{airreferencesubtracted}} \quad (5)$$

In one embodiment of the present invention, step 13205 is utilized to normalize the TIR data set. The signal processor 527 normalizes the reflectivity data set by dividing the reflectivity data set by the average value of the intensity of a set of pixels located in the middle portion of the peak area of the reflectivity data set (see FIG. 15c and FIG. 15d).

Figure 17A:
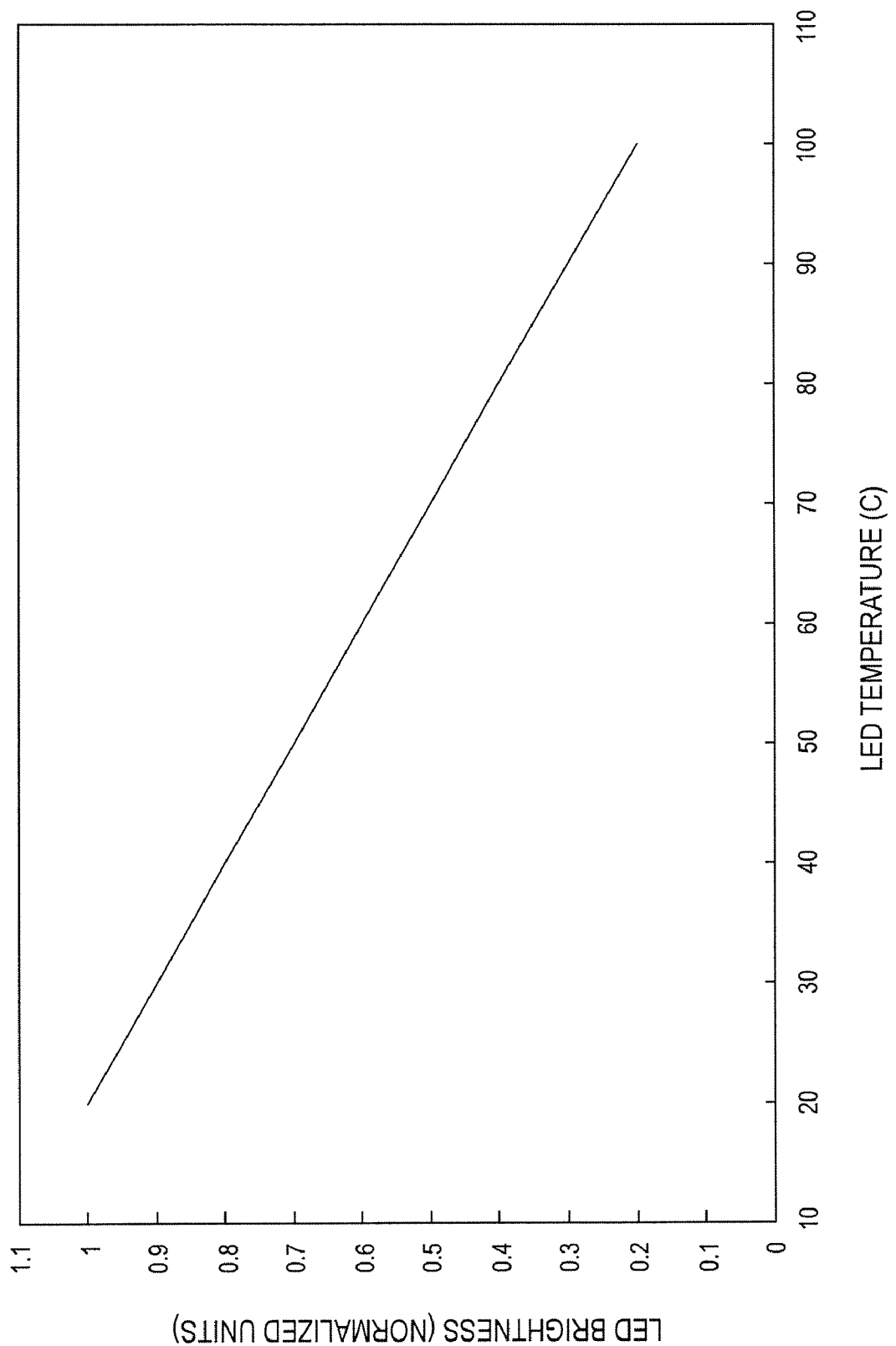
FIG. 17a illustrates LED brightness versus LED temperature data according to an embodiment of the present invention.

Alternatively, according to a second embodiment, step 13206 may be utilized to normalize the TIR data set. This involves an automated adjustment of LED light source brilliance. FIG. 17a illustrates a linear relationship between normalized LED brightness and LED temperature according to an embodiment of the present invention. The graph shows normalized LED brightness plotted as a function of LED temperature for a given LED. For typical LEDs available for use in embodiments of the present invention, the LED temperature changes diminish LED brightness by approximately a 10% decrease in LED brightness for every 10° C.

Figure 17B:
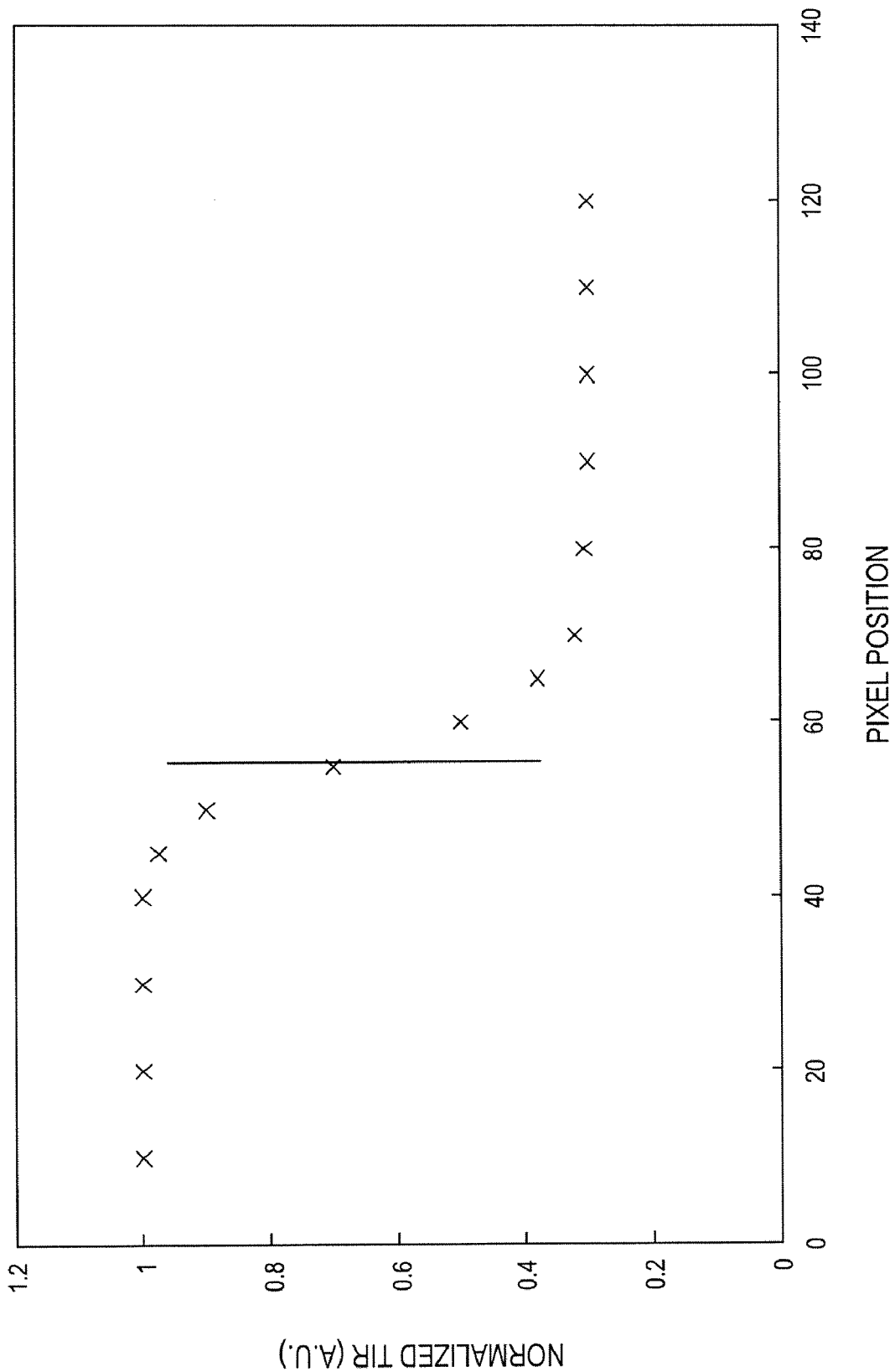
FIG. 17b illustrates the normalized total internal reflection with nominal LED brightness versus pixel position according to an embodiment of the present invention.
Figure 17C:
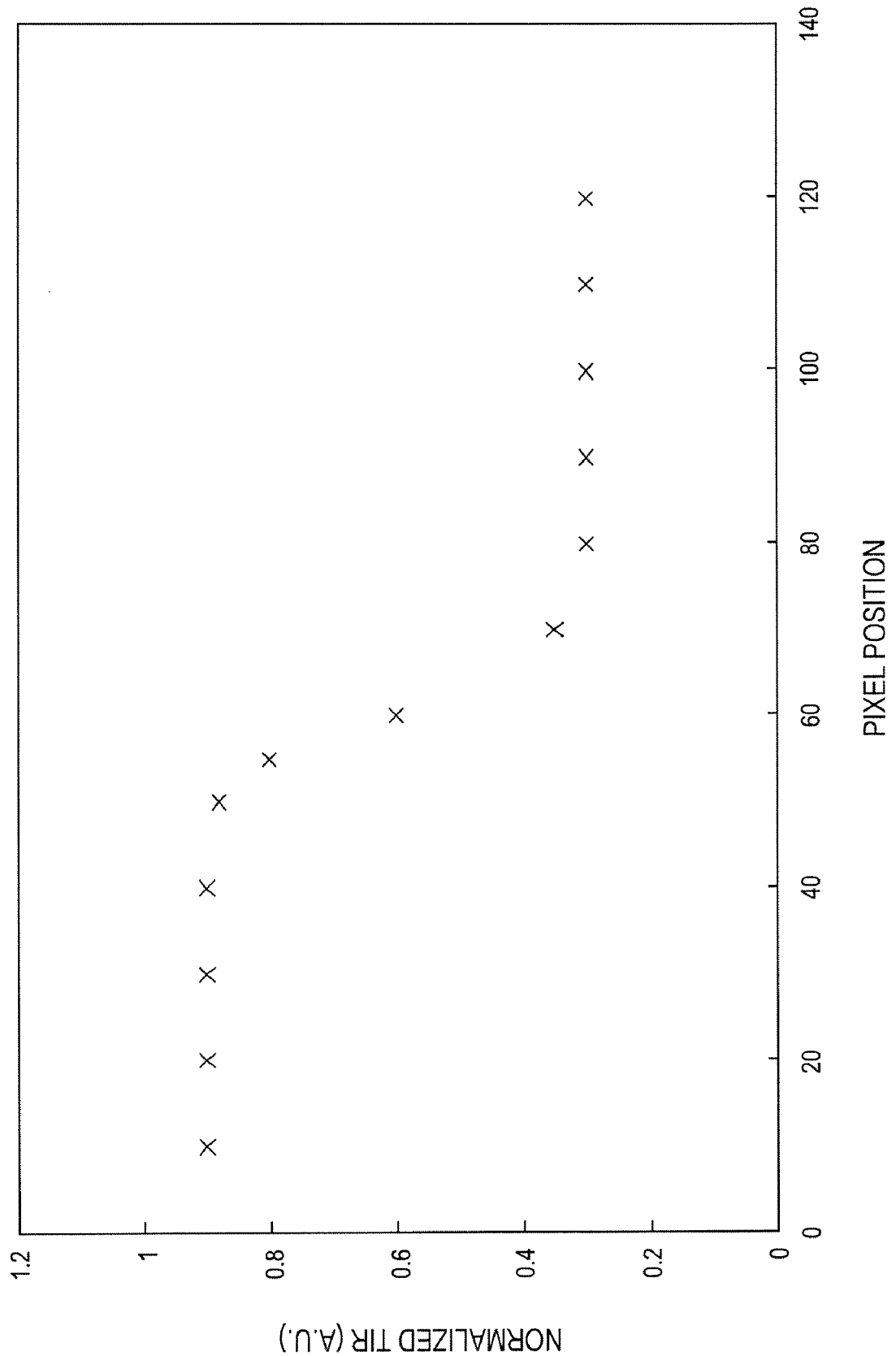
FIG. 17c illustrates the effect of LED temperature on normalized total internal reflection versus pixel position according to an embodiment of the present invention.

Referring to FIG. 17b, the idealized case of zero effect of LED brightness changes on TIR (total light intensity reflected) value is flat with a normalized average value equal to 1.0 out to the shadow line. The shadow line may be thought of as the rapid downward drop of the TIR data set in a liquid. Referring to FIG. 17c, the effect of LED temperature change on normalized TIR value is shown. In this case, the normalized TIR value is flat, but the normalized average TIR value has decreased from 1.0 to 0.9. The decrease in normalized TIR value may be compounded because the derivative of the normalized TIR value is used in the MM Algorithm. The cumulative effect is a loss of calibration and significant decrease in accuracy for IoR measurements and therefore concentration analysis of liquids.

Figure 17D:
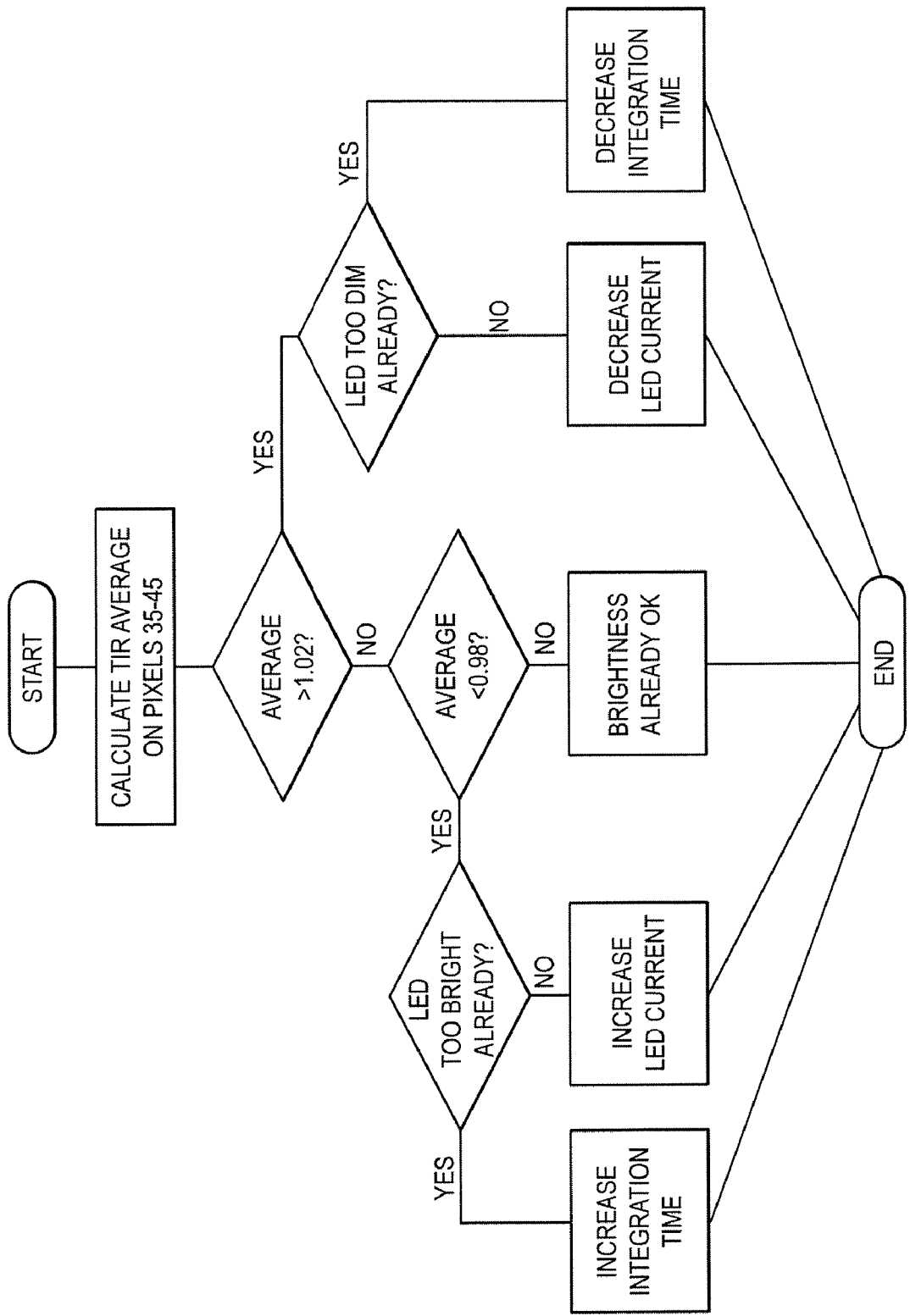
FIG. 17d illustrates a flow chart diagram of a method of automatic light level compensation and correction for LED intensity using an algorithm according to an embodiment of the present.

Embodiments of the present invention automatically correct and compensate for LED brightness changes. Referring to FIG. 17d, a flow chart diagram illustrates a method for automatic LED brightness correction and compensation. Depending on the average TIR value, the firmware algorithm automatically adjusts the LED brightness. This can be accomplished by adjusting the LED current up or down (usual case) or by changing the integration time of the photodetector array, so that light emitting from the LED illuminates for a longer (or shorter) time on the photodetector array 110. In both cases, the LED brightness is automatically adjusted to match a value established during the initialization of the optical sensor 300.

Referring to FIG. 13b, the next step 13207 involves the signal processor 527 calculating a pixel number using a numerical first derivative of the normalized total internal reflectivity (TIR) data ($S_i$) and a Mass Moment (MM) Algorithm.

The TIR data is numericially differentiated via a "smooth derivative" procedure:

$$S_i = \frac{\sum_{k=-4}^{4} k * TIR_{i+k}}{60} \quad (6)$$

Where the range of k and the number 60 determine the degree of smoothness.

The algorithm used is a weighted Mass Moment (MM) calculation. The weighted MM is shown in the equations below:

$$MW = \frac{\sum_{i=a}^{b} i \times Y_i}{\sum_{i=a}^{b} Y_i} \quad (7)$$

$$Y_i = \text{Ln}[1 + \exp(100 \times (S_i - T_h))] - \text{Ln}[1 + \exp(100 \times (0 - T_h))] \quad (8)$$

The weighted MM calculation gives more weight or emphasis to pixels near the mass moment pixel position of the first derivative. The values a and b are pixel numbers determined by empirical means that include the minimum of the numerical first derivative (see FIG. 18), $T_h$ is a threshold value that is also determined empirically and typically set to −0.03. Pixel numbers with corresponding first derivative values above $T_h$ are not include in the MM algorithm (equation (7)).

Figure 18:
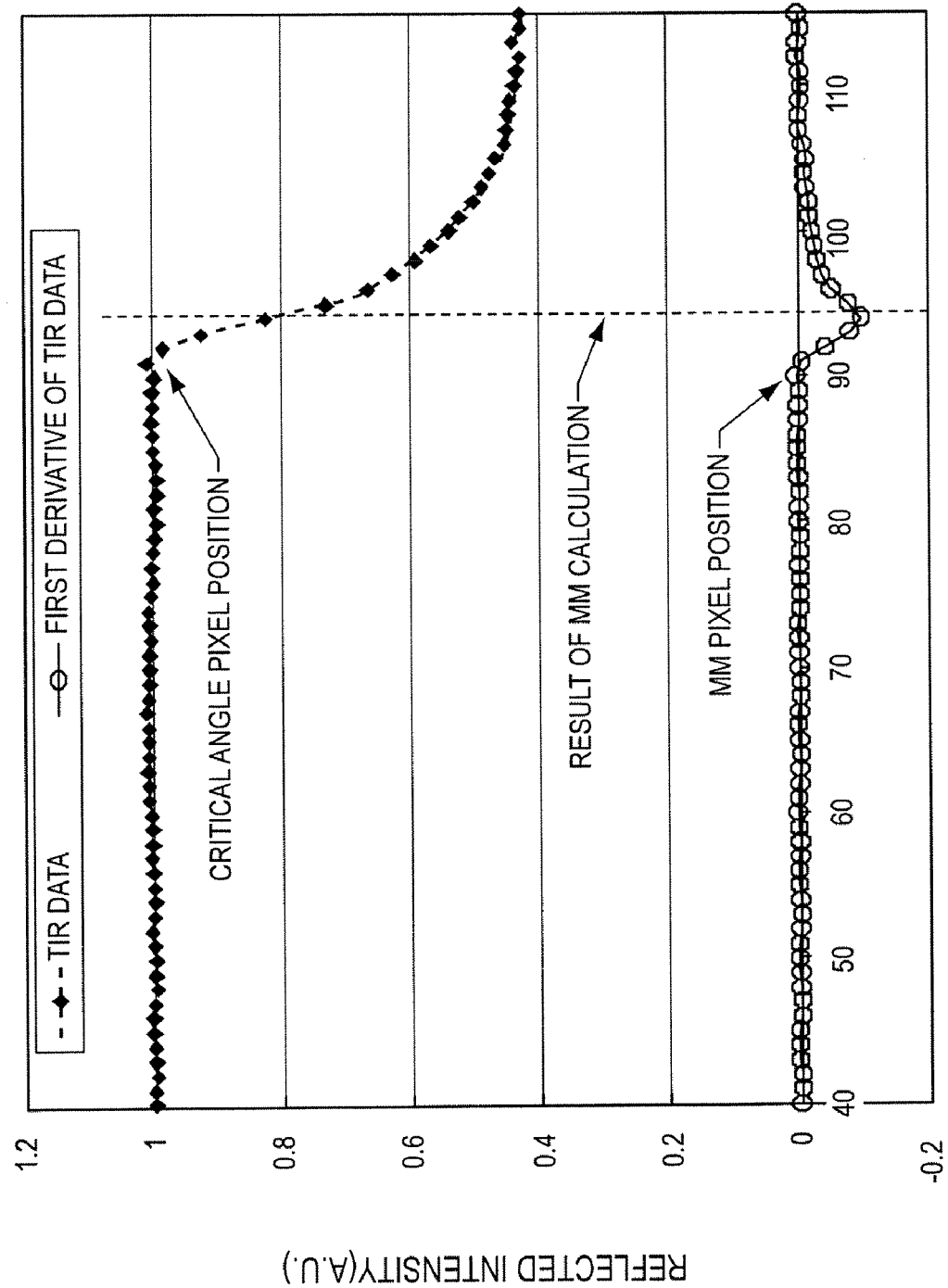
FIG. 18 illustrates normalized total internal reflection (TIR) data and the numerical first derivative of the TIR data plotted as a function of pixel number according to an embodiment of the present.

The MM value is shown in FIG. 18. For purposes of clarity it is shown that the MM value is not equal to the "drop off" edge of the TIR data. The drop off edge is generally considered to be at or very near the critical angle value. In the present invention, the critical angle value need not be determined. Instead a MM value of the numerical first derivative of the TIR data is determined. The MM value represents a pixel number value as see in FIG. 18. In the present invention, the MM value is used in calibration methods of the present invention to determine IoR and thereby chemical concentration. In this way, the present invention makes use of numerical operations and methods performed on the TIR data to determine IoR and need not rely on or make use of determination of the critical angle value. See, for example, FIG. 10 for the calibration method to convert MM pixel number values into IoR.

Figure 16C:
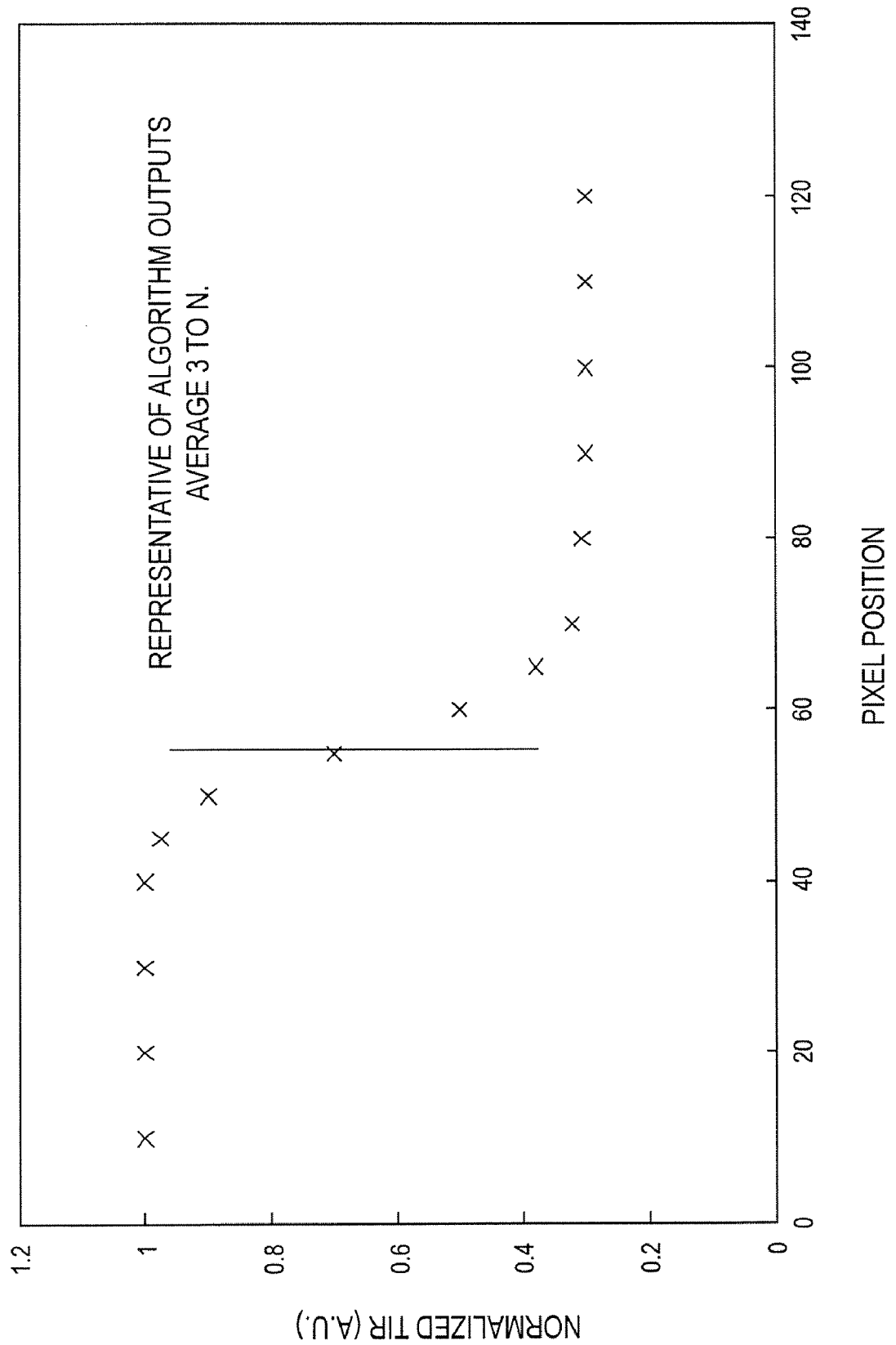

Referring to FIG. 13*b*, the next step 13208 involves "looping" steps 13201-13207 to determine an average value of a MM pixel position correlating to an IoR. Referring to FIG. 16*c*, the final stage of the data signal analysis averaging is illustrated. In the final stage of averaging three outputs of the data acquisition algorithm (see above) may be averaged. The final stage is post algorithm. The algorithm is run on the averaged raw data sets. Each data set results in a new pixel position. Multiple pixel positions are averaged together to obtain a final pixel position. The final stage helps to deal with noise caused by taking the derivative of a noisy signal, with losses due to floating point rounding errors, and due to noise inherent in any type of measurement. The three-stage signal averaging and data averaging is a key to obtaining improved resolution and accuracy from noisy inputs.

Figure 10:
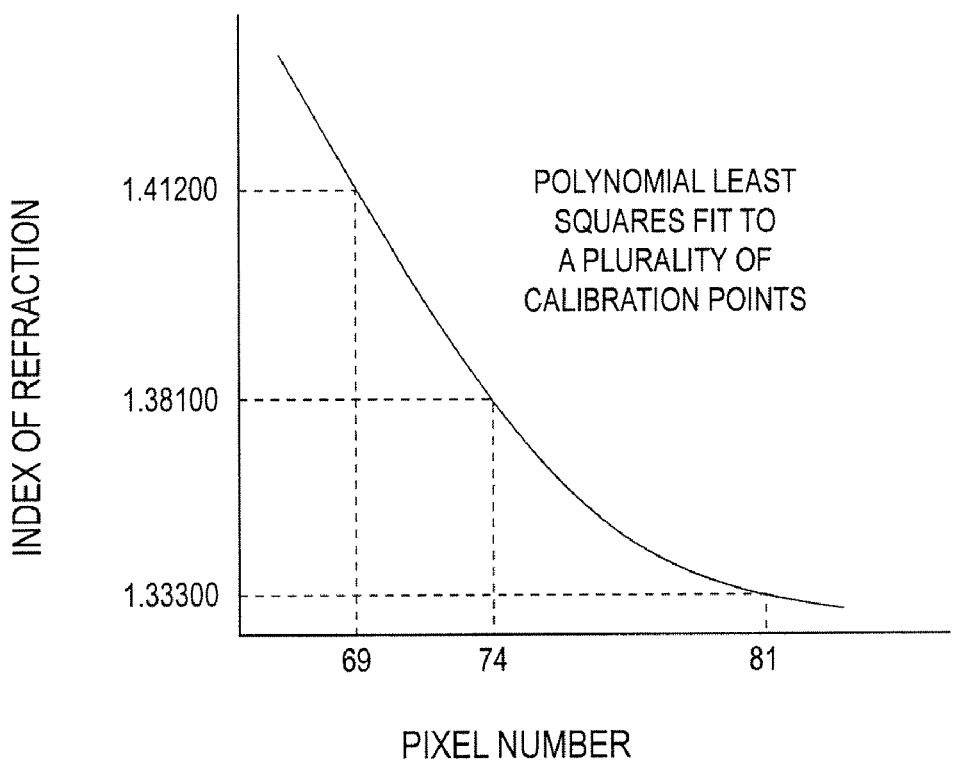
FIG. 10 illustrates a calibration of the measured Index of Refraction according to an embodiment of the present invention.

Referring to FIG. 13*b*, the next method step 13209 involves using the calibration curve shown in FIG. 10 generated during step 13102 to convert pixel position to IoR. Referring to FIG. 13*b*, there are two options for the next two steps in the method. In one embodiment, step 13210 and equation (2) are used to perform thermal compensation of IoR and to obtain $IoR_{TC}$. In an alternative embodiment, step 13211 is used for thermal compensation. Step 13211 illustrates the thermal compensation method as described in FIG. 9*d*, FIG. 19*a*, and FIG. 19*b* and involves a combination of linear, non-linear and lead/lag filtering (for thermal fluctuations) parameters to perform thermal compensation. It should be noted that thermal compensation can be performed using IoR values or using concentration values. In yet another embodiment of the present invention, IoR can be converted to concentration prior to thermal compensation. In this embodiment, equation (3) as described above may be used for thermal compensation of concentration.

Referring to FIG. 13*b*, if step 13210 is used, the next step 13212 involves using the curves of FIG. 11 generated during step 13103 to convert temperature compensated IoR to concentration. Finally, steps 13213-13215 involve concentration (or IoR) and fluid temperature outputs via LCD display, analog and digital signal outputs.

An analysis system 500 has been defined that incorporates miniaturized sensor technology having fixed optics inside a rigid, self-contained sensor platform or housing. The analysis system 500 combines an assortment of communications interface 550 which permits the integrated miniaturized optical sensor 300 of optical sub-system 510 to be placed at or near the sample of interest without interference from field personnel.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An optical sensor for measuring a concentration of a sample of interest, comprising:
    an optical housing having a sensing surface that forms the interface between said optical sensor and the sample of interest;
    a first temperature sensor and a second temperature sensor, said first temperature sensor arranged to measure the temperature of said optical housing and said second temperature sensor arranged to measure the temperature of said sample of interest;
    a photodetector array coupled to said optical housing; and
    a light source coupled to said optical housing and spatially arranged to emit light in the direction of said sensing surface, a portion of said light being internally reflected off said interface between said optical sensor and the sample of interest as a function of first and second temperatures measured by said first temperature sensor and said second temperature sensor, respectively, and the concentration of said sample of interest,
    said portion of said light being internally reflected to said photodetector array to determine the intensity thereof, wherein said intensity, and said first and second temperatures are utilized to calculate the concentration.

2. The optical sensor as recited in claim 1, wherein said first temperature sensor is embedded in said housing.

3. The optical sensor as recited in claim 2, further comprising an optical window positioned between said sensing surface and said sample of interest such that a surface of the optical window forms said interface between said optical sensor and the sample of interest and wherein said second temperature sensor is disposed in close proximity to said sensing surface of said housing and on said optical window.

4. The optical sensor as recited in claim 1, wherein said housing is composed of a material having a higher Index of Refraction than the sample of interest.

5. The optical sensor as recited in claim 1, wherein said housing is composed of light transmissive epoxy material.

6. The optical sensor as recited in claim 1, wherein said housing has a substantially pyramidal shape.

7. The optical sensor as recited in claim 1, wherein said housing has a substantially trapezoidal shape.

8. The optical sensor as recited in claim 1, wherein said photodetector array is a solid state linear photodiode array.

9. The optical sensor as recited in claim 1, further including a light reflective surface spatially inside said housing to direct light towards said photodetector array.

10. The optical sensor as recited in claim 9, wherein said light reflective surface is a planar surface.

11. The optical sensor as recited in claim 9, wherein said light reflective surface is a concave surface.

12. The optical sensor as recited in claim 1, wherein said sensing surface includes an optical window made from a material selected from the group consisting of quartz, sapphire, and glass.

13. The optical sensor as recited in claim 1, further including a signal processing unit coupled to a surface of a substrate and electronically connected to said photodetector array.

14. The optical sensor as recited in claim 13, wherein the signal processing unit is preprogrammable.

15. The optical sensor as recited in claim 1, further including a plurality of conductive leads coupled to an exterior surface of a substrate and forming conductive pathways to said photodetector array.

16. The optical sensor as recited in claim 1, wherein the intensity of said portion of said light being internally reflected is normalized by adjusting said photodetector array.

17. The optical sensor as recited in claim 1, wherein the intensity of said portion of said light being internally reflected is normalized by adjusting said light source.

18. An optical sensor system for measuring a concentration of a sample of interest, comprising:

a first temperature sensor and a second temperature sensor;

an optical housing having a sensing surface that forms the interface between said optical sensor and the sample of interest; said first temperature sensor arranged to measure the temperature of said optical housing and said second temperature sensor arranged to measure the temperature of said sample of interest, a photodetector array coupled to said optical housing;

a light source coupled to said optical housing and spatially arranged to emit light in the direction of said sensing surface, wherein a portion of said light is internally reflected off said sensing surface as a function of first and second temperatures measured by said first temperature sensor and said second temperature sensor, respectively, and the concentration of said sample of interest, said portion of said light being internally reflected to said photodetector array to determine the intensity thereof; and a signal processing unit to calculate the concentration of said sample of interest based on said first and second temperatures measured by said first temperature sensor and said second temperature sensor and a measured Index of Refraction of said sample of interest.

19. The optical sensor system as recited in claim 18, wherein the intensity of said portion of said light being internally reflected is normalized by adjusting said light source.

20. The optical sensor system as recited in claim 18, wherein the intensity of said portion of said light being internally reflected is normalized by adjusting said photodetector array.

21. The optical sensor system as recited in claim 18, wherein said housing is composed of light transmissive epoxy material.

22. The optical sensor system as recited in claim 18, wherein said housing has a substantially pyramidal shape.

23. The optical sensor system as recited in claim 18, wherein said housing has a substantially trapezoidal shape.

24. The optical sensor system as recited in claim 18, wherein said photodetector array is a solid state linear photodiode array.

25. The optical sensor system as recited in claim 18, further including a light reflective surface spatially inside said housing to direct light towards said photodetector array.

26. The optical sensor system as recited in claim 25, wherein said light reflective surface is a planar surface.

27. The optical sensor system as recited in claim 25, wherein said light reflective surface is a concave surface.

28. The optical sensor system as recited in claim 18, wherein said sensing surface includes an optical window made from a material selected from the group consisting of quartz, sapphire, and glass.

29. The optical sensor system as recited in claim 18, wherein said signal processing unit is selected from the group consisting of a digital signal processor, a PC-104 based microcontroller, and a microprocessor.

30. The optical sensor system as recited in claim 29, wherein the signal processing unit is preprogrammable.

31. The optical sensor system as recited in claim 18, further including a plurality of conductive leads coupled to an exterior surface of a substrate and forming conductive pathways to said photodetector array.

32. The optical sensor system as recited in claim 18, wherein said first temperature sensor is embedded in said housing.

33. The optical sensor system as recited in claim 32, wherein said second temperature sensor is disposed in close proximity to said sensing surface of said housing.

34. An optical sensor for measuring a concentration of a sample of interest using the positional intensity of incident light reflected from an interface between the optical sensor and the sample of interest, the optical sensor comprising:

a substrate having an interior surface and an exterior surface;

an optical housing coupled to said substrate and having a sensing surface including an optical window that forms the interface between said optical sensor and the sample of interest, said optical housing also having a first surface, the first surface forming a front face of a reflective mirror, the reflective mirror spatially arranged to receive light from said sensing surface and direct it towards said interior surface, said optical housing made of a single piece of material with a refractive index selected for its known relation to a refractive index of said sample of interest;

a first temperature sensor and a second temperature sensor;

a photodetector array coupled to said interior surface of said substrate and enclosed in said optical housing to receive light from said reflective mirror; and a light source coupled to said interior surface of said substrate adjacent said photodetector array, said light source enclosed in said optical housing and spatially arranged inside said optical housing to emit light in the direction of said sensing surface, wherein a portion of said light is internally reflected off said sensing surface as a function of first and second temperatures measured by said first temperature sensor and said second temperature sensor, respectively, and the concentration of said sample of interest, said portion of said light being internally reflected to said reflective mirror and then to said photodetector array to determine the intensity thereof, wherein said intensity, and said first and second temperatures are utilized to calculate the concentration.

35. The optical sensor as recited in claim 34, wherein said first temperature sensor is embedded in said housing.

36. The optical sensor as recited in claim 35, wherein said second temperature sensor is disposed in close proximity to said sensing surface of said housing.

37. The optical sensor as recited in claim 34, wherein said photodetector array is a linear photodiode array.

38. The optical sensor as recited in claim 34, wherein said housing has an optical geometry that allows light from said light source to strike said sensing surface and reflect off said sensing surface to strike said photodetector array.

39. The optical sensor as recited in claim 34, wherein said housing is composed of a medium with a higher Index of Refraction as compared to the sample of interest.

40. The optical sensor as recited in claim 34, wherein said first surface is a planar surface.

41. The optical sensor as recited in claim 34, wherein said optical window is made from a material selected from the group consisting of quartz, sapphire, and glass.

42. An optical sensor system comprising:

a first temperature sensor and a second temperature sensor;

a substrate having an interior surface with at least one light emitting diode and a photodetector array coupled thereto and a exterior surface with a plurality of signal pins extending therefrom;

a unitary light transmissive optical housing made from a single piece of material coupled to said substrate in an encapsulating manner over said interior surface, said housing integrally encapsulating said at least one light emitting diode and said photodetector array, said housing having a first surface and a sensing surface, wherein said first surface forms the front face of a reflective mirror, the reflective mirror is predisposed to receive light from said sensing surface and direct it towards said photodetector array, said sensing surface is predisposed to receive light from said light emitting diode, and wherein a portion of said received light is internally reflected off said sensing surface as a function of first and second temperatures measured by said first temperature sensor and said second temperature sensor, respectively, and the concentration of said sample of interest, said portion of said light being internally reflected to said reflective mirror and then to said photodetector array to determine the intensity thereof; and a signal processing unit to calculate the concentration of said sample of interest based on the first and second temperatures measured by said first temperature sensor and said second temperature sensor and a measured Index of Refraction of said sample of interest.

43. The optical sensor system as recited in claim 42, wherein the signal processing unit is electronically interconnected to said photodetector array by said plurality of signal pins.

44. The optical sensor system as recited in claim 43, wherein the signal processing unit is pre-programmable.

45. The optical sensor system as recited in claim 44, wherein said photodetector array is a solid state linear photodiode array.

46. The optical sensor system as recited in claim 42, wherein said first temperature sensor is embedded in said housing.

47. The optical sensor system as recited in claim 46, wherein said second temperature sensor is disposed in close proximity to said sensing surface of said housing.

48. The optical sensor system as recited in claim 42, wherein said signal processing unit is selected from the group consisting of a digital signal processor, a PC-104 based microcontroller, and a microprocessor.

* * * * *